(12) United States Patent
Kennedy et al.

(10) Patent No.: US 9,554,888 B2
(45) Date of Patent: Jan. 31, 2017

(54) PHASE SEPARATION SPRAYED SCAFFOLD

(75) Inventors: James P. Kennedy, Salt Lake City, UT (US); Robert Hitchcock, Sandy, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 732 days.

(21) Appl. No.: 13/642,439

(22) PCT Filed: Oct. 29, 2010

(86) PCT No.: PCT/US2010/054660
§ 371 (c)(1),
(2), (4) Date: Feb. 28, 2013

(87) PCT Pub. No.: WO2011/133183
PCT Pub. Date: Oct. 27, 2011

(65) Prior Publication Data
US 2013/0158650 A1    Jun. 20, 2013

Related U.S. Application Data

(60) Provisional application No. 61/326,054, filed on Apr. 20, 2010.

(51) Int. Cl.
*A61F 2/02* (2006.01)
*A61F 2/06* (2013.01)
*C07D 401/04* (2006.01)

(52) U.S. Cl.
CPC .............. *A61F 2/06* (2013.01); *C07D 401/04* (2013.01)

(58) Field of Classification Search
CPC .......... A61F 2/105; A61F 2/0063; A61F 2/06; C12N 2533/00; Y10T 29/49885; Y10T 29/4981; C07D 401/04; G01N 2203/0254; G01N 2203/0282; G01N 2203/0016; G01N 2203/0278; G01N 3/08; G01N 3/32; B29C 55/10; B29K 2027/18; Y10S 425/053; Y10S 428/91
(Continued)

(56) References Cited

U.S. PATENT DOCUMENTS 3,047,444 A * 7/1962 Harwood ................. D04H 1/66
156/291
4,482,516 A * 11/1984 Bowman ............... B29C 55/005
264/127
(Continued)

FOREIGN PATENT DOCUMENTS

| WO | WO 2008/134807 | 11/2008 |
|----|----------------|---------|
| WO | WO PCT/US2010/054660 | 10/2010 |
| WO | WO 2011/133183 | 10/2011 |

OTHER PUBLICATIONS

U.S. Appl. No. 61/326,054, filed Apr. 20, 2010, James P. Kennedy.
(Continued)

*Primary Examiner* — Katherine M Shi
*Assistant Examiner* — Mohamed Gabr
(74) *Attorney, Agent, or Firm* — Ballard Spahr LLP

(57) ABSTRACT

Systems and methods for producing scaffolds are disclosed. The system includes a polymer solution and a non-solvent, which are sprayed into receiving portions of support elements. After scaffolds are formed on the support elements, the support elements permit elongation of the scaffolds. Composites formed from a plurality of scaffolds are also disclosed.

36 Claims, 17 Drawing Sheets

(58) Field of Classification Search
USPC ...... 623/1.15, 23.74, 23.72, 23.71; 435/395; 264/299, 309, 310; 427/2.24; 424/423
See application file for complete search history.

(56) References Cited

U.S. PATENT DOCUMENTS

| | | | | |
|---|---|---|---|---|
| 4,677,854 | A * | 7/1987 | Gabelli | B29C 55/10 73/794 |
| 5,387,621 | A * | 2/1995 | Soldani | A61L 27/14 521/155 |
| 5,468,138 | A * | 11/1995 | Bosse | B29C 55/10 425/383 |
| 5,529,830 | A * | 6/1996 | Dutta | A41D 31/02 428/152 |
| 5,685,757 | A * | 11/1997 | Kirsch | D04H 5/06 428/903 |
| 5,827,246 | A * | 10/1998 | Bowen | A61M 1/008 604/313 |
| 6,103,255 | A | 8/2000 | Levene | 424/426 |
| 6,165,217 | A * | 12/2000 | Hayes | A61L 31/06 428/36.4 |
| 6,247,370 | B1 | 6/2001 | Ramaswamy | G01N 3/08 73/798 |
| 6,284,758 | B1 | 9/2001 | Egi | 514/252.03 |
| 6,337,198 | B1 | 1/2002 | Levene | 435/174 |
| 6,440,164 | B1 * | 8/2002 | DiMatteo | A61F 2/2412 623/1.24 |
| 6,557,651 | B1 * | 5/2003 | Norby | F16L 15/003 175/52 |
| 7,335,265 | B1 * | 2/2008 | Hossainy | B05D 1/002 118/307 |
| 9,134,209 | B2 * | 9/2015 | Brodland | G01N 3/04 |
| 2002/0142413 | A1 | 10/2002 | Brady | 435/395 |
| 2003/0082977 | A1 * | 5/2003 | Kuroiwa | B29C 55/08 442/328 |
| 2003/0204270 | A1 * | 10/2003 | Berman | A61L 17/04 623/23.64 |
| 2004/0052861 | A1 * | 3/2004 | Hatcher | A61L 27/446 424/602 |
| 2004/0254601 | A1 * | 12/2004 | Eskuri | 606/200 |
| 2005/0008675 | A1 * | 1/2005 | Bhatia | B29C 67/202 424/426 |
| 2005/0049566 | A1 * | 3/2005 | Vukos | A61F 13/15699 604/378 |
| 2005/0106717 | A1 * | 5/2005 | Wilson | C12M 23/08 435/297.5 |
| 2005/0209687 | A1 * | 9/2005 | Sitzmann | A61F 2/02 623/1.41 |
| 2006/0041247 | A1 * | 2/2006 | Petrosenko | A61F 13/00 604/543 |
| 2006/0195179 | A1 * | 8/2006 | Sun | A61L 27/38 623/1.54 |
| 2006/0269475 | A1 * | 11/2006 | Ryu | A61K 51/1282 424/1.11 |
| 2007/0009570 | A1 | 1/2007 | Kim | 424/426 |
| 2007/0027554 | A1 * | 2/2007 | Biran | A61L 31/146 623/23.74 |
| 2007/0049888 | A1 * | 3/2007 | Soerens | A61F 13/53 604/372 |
| 2007/0135606 | A1 * | 6/2007 | Belcheva | C08G 18/10 528/44 |
| 2007/0155010 | A1 * | 7/2007 | Farnsworth | A61L 27/18 435/399 |
| 2007/0180927 | A1 * | 8/2007 | Brodland | G01N 3/04 73/849 |
| 2007/0293112 | A1 * | 12/2007 | Hanson | B32B 3/28 442/381 |
| 2007/0298123 | A1 * | 12/2007 | Hunter | A61K 9/0019 424/646 |
| 2008/0195123 | A1 * | 8/2008 | Gainor | A61B 17/0057 606/151 |
| 2008/0217807 | A1 * | 9/2008 | Lee | B01D 39/1623 264/172.18 |
| 2008/0254125 | A1 * | 10/2008 | Freier | A61K 9/0024 424/488 |
| 2009/0163612 | A1 * | 6/2009 | Brady | A61L 29/06 521/170 |
| 2009/0216168 | A1 * | 8/2009 | Eckstein | A61F 13/00063 602/43 |
| 2011/0177590 | A1 * | 7/2011 | Clyne | A61L 27/38 435/325 |
| 2011/0287122 | A1 * | 11/2011 | Kim | C12N 5/0062 425/174.8 R |
| 2012/0179237 | A1 * | 7/2012 | Milner | B29C 41/003 623/1.15 |
| 2012/0253472 | A1 * | 10/2012 | Priewe | A61L 27/14 623/23.72 |
| 2012/0315830 | A1 * | 12/2012 | Joseph | B24B 37/26 451/59 |

OTHER PUBLICATIONS

International Preliminary Report on Patentability mailed Nov. 1, 2012 for PCT/US2010/054660 filed Oct. 29, 2010 and published as WO 2011/133183 on Oct. 27, 2011 (Inventors—Kennedy et al. // Applicant—University of Utah Research Foundation) (11 pages).
International Preliminary Report on Patentability mailed Feb. 10, 2011 for PCT/US2010/054660 filed Oct. 29, 2010 and published as WO 2011/133183 on Oct. 27, 2011 (Inventors—Kennedy et al. // Applicant—University of Utah Research Foundation) (12 pages).
Ayres C.E., et al. (2008) Measuring fiber alignment in electrospun scaffolds: a user's guide to the 2D fast Fourier transform approach. J. Biomater. Sci. Polym. Ed., 19(5):603-621.
Baker B.M., et al. (2008) The potential to improve cell infiltration in composite fiber-aligned electrospun scaffolds by the selective removal of sacrificial fibers. Biomaterials, 29(15):2348-2358.
Boukerrou M., et al. (2007) Study of the biomechanical properties of synthetic mesh implanted in vivo. Eur. J. Obstet. Gynecol. Reprod. Biol., 134(2):262-267.
Camelliti P. (2006) Structural and functional coupling of cardiac myocytes and fibroblasts. Adv. Cardiol., 42:132-149.
Caquineau H., et al. (2003) Influence of the relative humidity on film formation by vapor induced phase separation. Polymer Engineering & Science, 43(4):798-808.
Carrier R.L., et al. (2002) Perfusion improves tissue architecture of engineered cardiac muscle. Tissue Engineering, 8(2):175-188.
Charles-Harris M., et al. (2007) Mechanical and structural characterisation of completely degradable polylactic acid/calcium phosphate glass scaffolds. Biomaterials, 28(30):4429-4438.
Chilton L., et al. (2007) Evidence of intercellular coupling between co-cultured adult rabbit ventricular myocytes and myofibroblasts. J. Physiol., 583(Pt 1):225-236.
Costa K, et al. (2003) Creating alignment and anisotropy in engineered heart tissue: role of boundary conditions in a model three-dimensional culture system. Tissue Eng., 9(4):567-577.
Courtney T., et al. (2006) Design and analysis of tissue engineering scaffolds that mimic soft tissue mechanical anisotropy. Biomaterials, 27(19):3631-3638.
Dar A, et al. (2002) Cardiac tissue engineering Optimization of cardiac cell seeding and distribution in 3D porous alginate scaffolds. Biotechnol. Bioeng., 80(3):305-312.
Den Buijs J.O., et al. (2009) Cyclic Deformation-Induced Solute Transport in Tissue Scaffolds with Computer Designed, Interconnected, Pore Networks: Experiments and Simulations. Ann Biomed Eng., 37(8):1601-1612.
Den Buijs J.O., et al. (2009) Solute Transport in Cyclically Deformed Porous Tissue Scaffolds with Controlled Pore Cross-Sectional Geometries. Tissue Engineering Part A., 15(8):1989-1999.
Engelmayr G.C., Jr., et al. (2008) Accordion-like honeycombs for tissue engineering of cardiac anisotropy. Nat. Mater., 7(12):1003-1010.
Eschenhagen T, et al. (2005) Engineering myocardial tissue. Circ. Res., 97(12):1220-1231.
Franklin M.E., Jr., et al. (2008) The use of porcine small intestinal submucosa as a prosthetic material for laparoscopic hernia repair in

(56) References Cited

OTHER PUBLICATIONS infected and potentially contaminated fields: long-term follow-up. Surg. Endosc.
Freed L.E., et al. (1994) Biodegradable Polymer Scaffolds for Tissue Engineering. Nat. Biotechnol., 12(7):689-693.
Fromstein J.D., et al. (2008) Seeding bioreactor-produced embryonic stem cell-derived cardiomyocytes on different porous, degradable, polyurethane scaffolds reveals the effect of scaffold architecture on cell morphology. Tissue Eng. Part A, 14(3):369-78.
Gilbert T.W., et al. (2008) Morphologic assessment of extracellular matrix scaffolds for patch tracheoplasty in a canine model. Ann. Thorac. Surg., 86(3):967-974; discussion 967-974.
Goldsmith EC, et al., (2004) Organization of fibroblasts in the heart. Dev. Dyn., 230(4).
Guido S. et al. (1993) A methodology for the systematic and quantitative study of cell contact guidance in oriented collagen gels. Correlation of fibroblast orientation and gel birefringence. J. Cell Sci., 105 (Pt 2):317-331.
Helm P.A., et al. (2005) Ex vivo 3D diffusion tensor imaging and quantification of cardiac laminar structure. Magn. Reson. Med., 54(4):850.
Hiltunen R., et al., (2007) Low-weight polypropylene mesh for anterior vaginal wall prolapse: a randomized controlled trial. Obstet. Gynecol., 110(2 Pt 2):455-462.
Hollister S.J. (2005) Porous scaffold design for tissue engineering. Nat. Mater., 4(7):518-524.
Huang N.F., et al. (2006) Myotube assembly on nanofibrous and micropatterned polymers. Nano Lett., 6(3):537-542.
Kennedy J.P., et al. (2010) The mechanically enhanced phase separation of sprayed polyurethane scaffolds and their effect on the alignment of fibroblasts. Biomaterials. 31(6):1126-1132.
Khorasani M.T., et al. (2006) Fabrication of microporous polyurethane by spray phase inversion method as small diameter vascular grafts material. J. Biomed. Mater. Res. A., 77(2):253-260.
Kim S.S., et al. (1998) Survival and function of hepatocytes on a novel three-dimensional synthetic biodegradable polymer scaffold with an intrinsic network of channels. Annals of Surgery, 228(1):8.
Kohl P., et al., (2005) Electrical coupling of fibroblasts and myocytes: relevance for cardiac propagation. J. Electrocardiol., 38(4 Suppl):45-50.
Kreitz M.R., et al. (1997) Controlled delivery of therapeutics from microporous membranes. I. Fabrication and characterization of microporous polyurethane membranes containing polymeric microspheres. Biomaterials, 18(8):597-603.
Kretzmer G., et al., (1991) Response of mammalian cells to shear stress. Applied Microbiology and Biotechnology, 34(5):613-616.
Lijnen P., et al. (2000) Induction of cardiac fibrosis by aldosterone. J. Mol. Cell Cardiol., 32(6):865-879.
Miragoli M., et al. (2006) Electrotonic modulation of cardiac impulse conduction by myofibroblasts. Circ. Res., 98(6):801-810.
Moroni L., et al. (2006) 3D fiber-deposited scaffolds for tissue engineering: influence of pores geometry and architecture on dynamic mechanical properties. Biomaterials, 27(7):974-985.
Moutos F.T., et al. (2007) A biomimetic three-dimensional woven composite scaffold for functional tissue engineering of cartilage. Nature Materials, 6(2):162-167.
Nicoletti A., et al. (1999) Cardiac fibrosis and inflammation: interaction with hemodynamic and hormonal factors. Cardiovasc. Res., 41(3):532-543.
Norman J.J., et al. (2005) Control of cellular organization in three dimensions using a microfabricated polydimethylsiloxane-collagen composite tissue scaffold. Tissue Eng., 11(3-4):378-386.
Okoshi T. (1995) New concept of microporous structure in small diameter vascular prostheses. Artif. Organs, 19(1):27-31.
Okoshi T., et al. (1992) Microporous small diameter PVDF-TrFE vascular grafts fabricated by a spray phase inversion technique. ASAIO J., 38(3):M201-206.
Ott H., et al. (2008) Perfusion-decellularized matrix: using nature's platform to engineer a bioartificial heart. Nature Medicine, 14(2):213-221.
Papenburg B., et al. (2007) One-step fabrication of porous micropatterned scaffolds to control cell behavior. Biomaterials, 28(11):1998-2009.
Park H., et al. (2005) A novel composite scaffold for cardiac tissue engineering. IIn Vitro Cell Dev Biol Anim., 41(7):188-196.
Radisic M, et al. (2007) Biomimetic approach to cardiac tissue engineering. Philos. Trans. R. Soc. Lond. B. Biol. Sci., 362(1484):1357.
Radisic M., et al., (2004) Medium perfusion enables engineering of compact and contractile cardiac tissue. Am J Physiol Heart Circ Physiol., 286(2):507-516.
Radisic M., et al., (2005) Mathematical model of oxygen distribution in engineered cardiac tissue with parallel channel array perfused with culture medium containing oxygen carriers. Am J Physiol Heart Circ Physiol., 288(3):1278-1289.
Rook M.B., et al. (1992) Differences in gap junction channels between cardiac myocytes, fibroblasts, and heterologous pairs. Am. J. Physiol., 263(5 Pt 1):C959-977 (Abstract).
Rowlands A.S., et al. (2007) Polyurethane/poly(lactic-co-glycolic) acid composite scaffolds fabricated by thermally induced phase separation. Biomaterials, 28(12):2109-2121.
Rudy Y. (2004) Conductive bridges in cardiac tissue: a beneficial role or an arrhythmogenic substrate? Circ. Res., 94(6):709-711.
Sachse F.B., et al. (2008) Electrophysiological modeling of fibroblasts and their interaction with myocytes. Ann. Biomed. Eng., 36(1):41-56.
Sachse F.B., et al. (2009) A model of electrical conduction in cardiac tissue including fibroblasts. Ann. Biomed. Eng., 37(5):874-889.
Sakai Y., et al. (2004) A novel poly-L-lactic acid scaffold that possesses a macroporous structure and a branching/joining three-dimensional flow channel network: its fabrication and application to perfusion culture of human hepatoma Hep G2 cells. Materials Science & Engineering C., 24(3):379-386.
Sands RW, et al. (Oct. 2007) Polymers to direct cell fate by controlling the microenvironment. Curr. Opin. Biotechnol., 18(5):448-453.
Simpson D et al. (1994) Modulation of cardiac myocyte phenotype in vitro by the composition and orientation of the extracellular matrix. J. Cell Physiol., 161(1).
Stankus J.J., et al. (2006) Microintegrating smooth muscle cells into a biodegradable, elastomeric fiber matrix. Biomaterials, 27(5):735-744.
Swaney J.S., et al. (2005) Inhibition of cardiac myofibroblast formation and collagen synthesis by activation and overexpression of adenylyl cyclase. Proc. Natl. Acad. Sci. U S A., 102(2):437-442.
Szycher M. et al. (1987) High Performance Tecoflex Polyurethanes in Biomedical Applications in *Advances in Biomaterials*. Published by Technomic Publishing Company (Lancaster, PA), pp. 110-118.
Tarhan E., et al. (2008) Comparison of AlloDerm, fat, fascia, cartilage, and dermal grafts in rabbits. Arch. Facial Plast. Surg., 10(3):187-193.
Tomasek J.J., et al. (2002) Myofibroblasts and mechano-regulation of connective tissue remodelling. Nature Reviews Molecular Cell Biology, 3(5):349-363.
Van Heugten H.A., et al. (1993) Homologous desensitization of the endothelin-1 receptor mediated phosphoinositide response in cultured neonatal rat cardiomyocytes. J. Mol. Cell Cardiol., 25(1):41-52.
Venugopal J, et al. (2008) Interaction of cells and nanofiber scaffolds in tissue engineering. J. Biomed. Mater. Res. B Appl. Biomater., 84(1):34-48.
Weber K.T., et al. (1993) Myocardial fibrosis: functional significance and regulatory factors. Cardiovasc. Res., 27(3):341-348.
Weber K.T., et al. (2003) Aldosteronism in heart failure: a proinflammatory/fibrogenic cardiac phenotype. Search for biomarkers and potential drug targets. Curr. Drug Targets, 4(6):505-516.
Wu M.P. (2008) The use of prostheses in pelvic reconstructive surgery: joy or toy? Taiwan J. Obstet. Gynecol., 47(2):151-156.
Xu C.Y., et al. (2004) Aligned biodegradable nanofibrous structure: a potential scaffold for blood vessel engineering. Biomaterials, 25(5):877-886. (Abstract).

(56) References Cited

OTHER PUBLICATIONS

Yan Y, et al. (2003) Layered manufacturing of tissue engineering scaffolds via multi-nozzle deposition. Materials Letters. 57(2003): 2623-22628.
Zeisberg E.M., et al. (2007) Endothelial-to-mesenchymal transition contributes to cardiac fibrosis. Nat Med., 13(8):952-961.
Zhang C., et al. (2008) Synthesis and characterization of biodegradable elastomeric polyurethane scaffolds fabricated by the inkjet technique. Biomaterials, 29(28):3781-3791.
Zlochiver S., et al. (2008) Electrotonic myofibroblast-to-myocyte coupling increases propensity to reentrant arrhythmias in two-dimensional cardiac monolayers. Biophys. J., 95(9):4469-4480.
Zong X., et al. (2005) Electrospun fine-textured scaffolds for heart tissue constructs. Biomaterials, 26(26):5330-5338.

\* cited by examiner

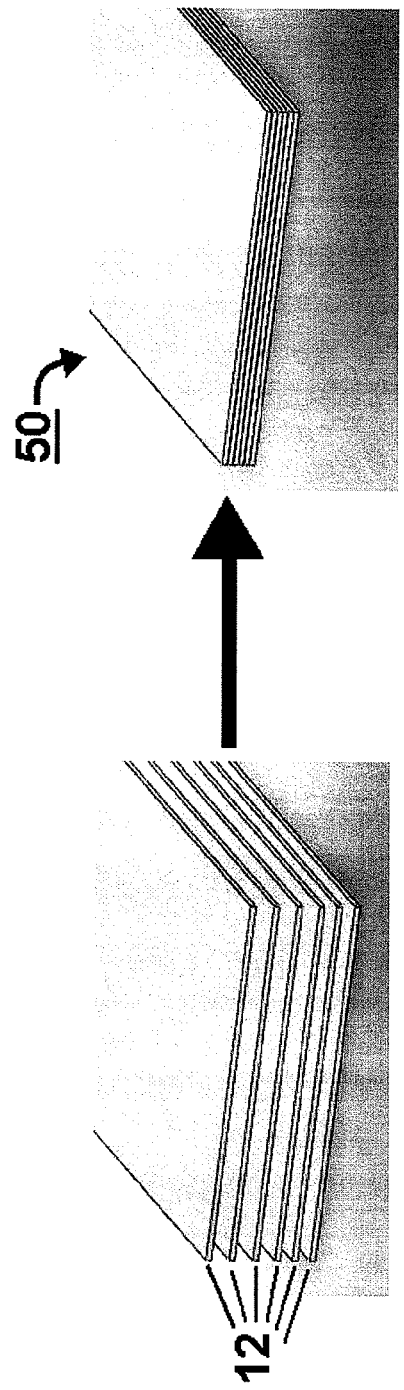

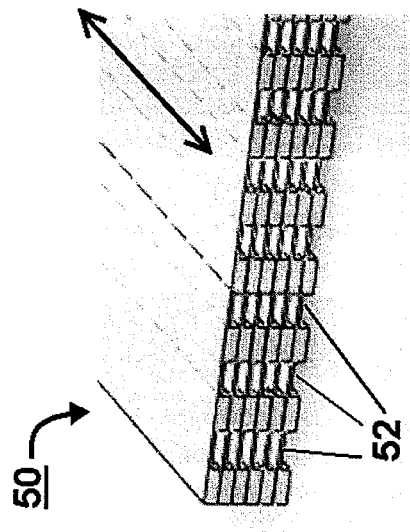
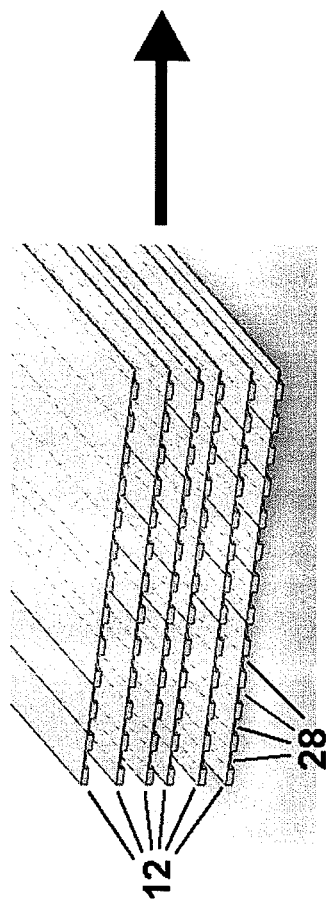
FIGURE 7A
FIGURE 7B

Effective modulus of elasticity in the preferred and transverse directions and corresponding ratio of anisotropy for each type of scaffold. Values are mean ± sd.

| Nonsolvent EtOH | Scaffold Elongation | Modulus (PD) (MPa) | Modulus (XD) (MPa) | Mechanical Anisotropy |
|---|---|---|---|---|
| 0% | 0% | 1.18 ± 0.02 | NA | NA |
| | 35% | 1.43 ± 0.07 | 1.18 ± 0.05 | 1.21 |
| | 70% | 1.53 ± 0.05 | 0.83 ± 0.05 | 1.85 |
| 50% | 0% | 0.32 ± 0.02 | NA | NA |
| | 35% | 0.46 ± 0.04 | 0.44 ± 0.03 | 1.04 |
| | 70% | 0.57 ± 0.03 | 0.27 ± 0.07 | 2.12 |
| 70% | 0% | 0.18 ± 0.03 | NA | NA |
| | 35% | 0.27 ± 0.05 | 0.22 ± 0.04 | 1.23 |
| | 70% | 0.36 ± 0.02 | 0.18 ± 0.03 | 2.05 |

FIGURE 16

PHASE SEPARATION SPRAYED SCAFFOLD

CROSS-REFERENCE TO RELATED APPLICATIONS

This application is a National Phase Application of International Application No. PCT/US2010/054660, filed Oct. 29, 2010, which claims priority to U.S. Patent Application No. 61/326,054, filed Apr. 20, 2010, which applications are incorporated herein fully by this reference.

BACKGROUND OF THE INVENTION

Field of the Invention

This invention relates to systems and methods for producing scaffolds and, more particularly, to systems and methods for producing scaffolds having desired physical properties.

Description of the Prior Art

Tissue engineering and regenerative medicine have the potential to develop novel biosynthetic materials for improved treatment, maintenance, and regeneration of diseased or damaged tissue. Development and design of materials that utilize tissue engineering strategies to mimic the functionality of native tissue requires consideration of cell type, seeding and attachment, molecular signals, and macromolecular matrix. See Sands R W, Mooney D J. *Polymers to direct cell fate by controlling the microenvironment*. Curr Opin Biotechnol 2007 October; 18(5):448-453; Freed L E, Vunjak-Novakovic G, Biron R J, Eagles D B, Lesnoy D C, Barlow S K, et al. *Biodegradable Polymer Scaffolds for Tissue Engineering*. Bio/Technology 1994; 12(7):689-693; Venugopal J, Low S, Choon A T, Ramakrishna S. *Interaction of cells and nanofiber scaffolds in tissue engineering*. J Biomed Mater Res B Appl Biomater 2008 January; 84(1): 34-48.

Many types of engineered tissue rely on a provisional or permanent scaffold to generate a three-dimensional framework for cell attachment and tissue organization. Both natural and synthetic scaffold materials are used in tissue engineering. See Ott H, Matthiesen T, Goh S, Black L, Kren S, Netoff T, et al. *Perfusion-decellularized matrix: using nature's platform to engineer a bioartificial heart*. Nature Medicine 2008; 14(2):213-221; Courtney T, Sacks M S, Stankus J, Guan J, Wagner W R. *Design and analysis of tissue engineering scaffolds that mimic soft tissue mechanical anisotropy*. Biomaterials 2006 July; 27(19):3631-3638. Synthetically derived cell scaffolds can be permanent or degradable and facilitate expression and organization of the extracellular matrix (ECM). Architectural cues in these scaffolds have been shown to affect the morphology, organization, and phenotypic expression of cells in vitro. See Engelmayr G C, Jr., Cheng M, Bettinger C J, Borenstein J T, Langer R, Freed L E. *Accordion-like honeycombs for tissue engineering of cardiac anisotropy*. Nat Mater 2008 December; 7(12):1003-1010; Fromstein J D, Zandstra P W, Alperin C, Rockwood D, Rabolt J F, Woodhouse K A. *Seeding bioreactor-produced embryonic stem cell-derived cardiomyocytes on different porous, degradable, polyurethane scaffolds reveals the effect of scaffold architecture on cell morphology*. Tissue Eng Part A 2008 March; 14(3):369-378; Guido S, Tranquillo R T. *A methodology for the systematic and quantitative study of cell contact guidance in oriented collagen gels: Correlation of fibroblast orientation and gel birefringence*. J Cell Sci 1993 June; 105 (Pt 2):317-331. In order to develop effective implants, tissue engineers need to be able to specify and tune the scaffold's morphological features for different applications. In addition, scaffold architecture must be designed to provide cues for cellular organization and form the basis for engineered tissue constructs that mimic tissue-specific organization and physical properties.

Cardiac tissue is an example of highly structured tissue that relies on cellular organization for its function. See Simpson D, Terracio L, Terracio M, Price R, Turner D, Borg T. *Modulation of cardiac myocyte phenotype in vitro by the composition and orientation of the extracellular matrix*. J Cell Physiol 1994; 161(1); Goldsmith E C, Hoffman A, Morales M O, Potts J D, Price R L, McFadden A, et al. *Organization of fibroblasts in the heart*. Dev Dyn 2004; 230(4). Cell scaffold materials can help cardiac tissue development by: (1) providing cues that induce alignment of cardiac myocytes; (2) allowing sufficient nutrient and cell infiltration necessary for forming a three-dimensional tissue construct; (3) modulating the cell type distribution of co-cultures; and (4) mimicking anisotropic mechanical stiffness of the heart. Scaffolds used for cardiac tissue engineering applications require development of design specifications for scaffold alignment, structure, porosity, and stiffness, all of which will influence cellular development, overall tissue organization, and bioreactor integration. See Eschenhagen T, Zimmermann W H. *Engineering myocardial tissue*. Circ Res 2005; 97(12):1220-1231; Charles-Harris M, del Valle S, Hentges E, Bleuet P, Lacroix D, Planell J A. *Mechanical and structural characterisation of completely degradable polylactic acid/calcium phosphate glass scaffolds*. Biomaterials 2007 October; 28(30):4429-4438; Radisic M, Park H, Gerecht S, Cannizzaro C, Langer R, Vunjak-Novakovic G. *Biomimetic approach to cardiac tissue engineering*. Philos Trans R Soc Lond B Biol Sci 2007; 362(1484):1357.

Various methods have been employed to fabricate scaffolds of varying porosities and anisotropies. For example, microfabrication techniques have been used to fabricate scaffolds with aligned structures. See Huang N F, Patel S, Thakar R G, Wu J, Hsiao B S, Chu B, et al. *Myotube assembly on nanofibrous and micropatterned polymers*. Nano Lett 2006 March; 6(3):537-542; Norman J J, Desai T A. *Control of cellular organization in three dimensions using a microfabricated polydimethylsiloxane-collagen composite tissue scaffold*. Tissue Eng 2005; 11(3-4):378-386. Electrospinning methods have been employed with post-process elongation to produce anisotropic fibrous scaffold architecture. Zong X, Bien H, Chung C Y, Yin L, Fang D, Hsiao B S, et al. *Electrospun fine-textured scaffolds for heart tissue constructs*. Biomaterials 2005 September; 26(26):5330-5338. In order to create scaffolds that allow adequate nutrient and oxygen diffusion, methods such as three-dimensional fiber deposition, sacrificial fiber electrospinning, and phase separation have been utilized to generate scaffolds of controlled porosities. See Hollister S J. *Porous scaffold design for tissue engineering*. Nat Mater 2005 July; 4(7):518-524; Baker B M, Gee A O, Metter R B, Nathan A S, Marklein R A, Burdick J A, et al. *The potential to improve cell infiltration in composite fiber-aligned electrospun scaffolds by the selective removal of sacrificial fibers*. Biomaterials 2008 May; 29(15):2348-2358; Khorasani M T, Shorgashti S. *Fabrication of microporous polyurethane by spray phase inversion method as small diameter vascular grafts material*. J Biomed Mater Res A 2006 May; 77(2):253-260; Moroni L, de Wijn J R, van Blitterswijk C A. *3D fiber-deposited scaffolds for tissue engineering: influence of pores geometry and architecture on dynamic mechanical properties*. Biomaterials 2006 March; 27(7):974-985. Spray phase separation (SPS) is method for creating scaffolds that permits control over alignment, porosity, and stiffness; however this method has not been directly applied for cardiac tissue scaffolds. See Khorasani M T, Shorgashti S. *Fabrication of microporous polyurethane by spray phase inversion method as small diameter vascular grafts material*. J Biomed Mater Res A 2006 May; 77(2):253-260.

SPS-fabricated scaffolds are produced using a method that sprays a polymer solution onto a surface while simultaneously spraying a nonsolvent onto the surface. The nonsolvent mixes with the solvent and the polymer causing the polymer to precipitate. Some groups have used SPS methods to fabricate materials of varying porosity for drug delivery devices and vascular graft materials. See Kreitz M R, Webber W L, Galletti P M, Mathiowitz E. *Controlled delivery of therapeutics from microporous membranes. I. Fabrication and characterization of microporous polyurethane membranes containing polymeric microspheres*. Biomaterials 1997 April; 18(8):597-603; Khorasani M T, Shorgashti S. *Fabrication of microporous polyurethane by spray phase inversion method as small diameter vascular grafts material*. J Biomed Mater Res A 2006 May; 77(2):253-260; Okoshi T, Chen H, Soldani G, Galletti P M, Goddard M. *Microporous small diameter PVDF-TrFE vascular grafts fabricated by a spray phase inversion technique*. ASAIO J 1992 July-September; 38(3):M201-206. SPS fabrication methods can be used to vary scaffold properties such as alignment, porosity, stiffness, and anisotropy, which are key features for directing cellular development, overall tissue organization, and bioreactor integration. See Eschenhagen T, Zimmermann W H. *Engineering myocardial tissue*. Circ Res 2005; 97(12):1220-1231; Charles-Harris M, del Valle S, Hentges E, Bleuet P, Lacroix D, Planell J A. *Mechanical and structural characterisation of completely degradable polylactic acid/calcium phosphate glass scaffolds*. Biomaterials 2007 October; 28(30):4429-4438; Radisic M, Park H, Gerecht S, Cannizzaro C, Langer R, Vunjak-Novakovic G. *Biomimetic approach to cardiac tissue engineering*. Philos Trans R Soc Lond B Biol Sci 2007; 362(1484):1357.

Accordingly, there is a need in the pertinent art for systems and methods of efficiently producing scaffolds having selectively adjustable mechanical properties. In particular, there is a need in the pertinent art for systems and methods of efficiently and accurately producing scaffolds having selected structural alignment, porosity, and stiffness. There is a further need in the pertinent art for systems and methods for producing composites formed from multiple scaffolds.

SUMMARY OF THE INVENTION

Described herein are systems and methods for producing scaffolds. In one aspect, a system for producing scaffolds comprises a polymer solution and a non-solvent. In another aspect, the system for producing scaffolds comprises support elements secured on a backing member. The support elements can have receiving portions for promoting adherence of a scaffold. The support elements are optionally configured to permit selective elongation of scaffolds that are adhered to the receiving portions. The receiving portions of the support elements can have corrugated outer surfaces that define channels in scaffolds that are adhered to the receiving portions. In an additional aspect, the system for producing scaffolds comprises a spraying machine that permits selective control of the spraying of the polymer solution and the non-solvent. Also disclosed are devices for producing scaffolds.

In one aspect, a method for producing scaffolds comprises securing support elements to the backing member. In another aspect, the method for producing scaffolds comprises simultaneously spraying the polymer solution and the non-solvent in the receiving portions of the support elements to thereby form a scaffold. Optionally, in an additional aspect, the method for producing scaffolds comprises elongating the scaffolds. The method for producing scaffolds can optionally comprise rinsing the scaffolds and drying the scaffolds.

The systems and methods described herein can also be used to produce a composite comprising multiple scaffolds positioned in a stacked relationship. Optionally, the composite can comprise a plurality of spaced perfusion channels positioned between contiguous scaffolds.

BRIEF DESCRIPTION OF TILE DRAWINGS

These and other features of the preferred embodiments of the invention will become more apparent in the detailed description in which reference is made to the appended drawings wherein:

FIG. 1 is a schematic depiction of a system for producing scaffolds, as described herein.

FIG. 2A is a top view of a frame for receiving scaffolds, as described herein. FIG. 2B is a bottom view of a frame after receiving a scaffold, as described herein. FIG. 2C is a bottom view of the frame of FIG. 2B following partial elongation of the scaffold. FIG. 2D is a bottom view of the frame of FIG. 2B following full elongation of the scaffold.

FIG. 3 is a top view of a frame for receiving scaffolds, as described herein.

FIG. 4A is a top view of an array of frames for receiving and elongating scaffolds, as described herein. FIG. 4B is a top view of the array of FIG. 4A following receipt of scaffolds and prior to elongation of the scaffolds. FIG. 4C is a top view of the array of FIG. 4A following elongation of the scaffolds.

FIG. 6A is a perspective view of a plurality of scaffolds prior to being placed in a stacked orientation, as described herein. FIG. 6B is a perspective view of a composite formed from the plurality of scaffolds of FIG. 6A.

FIG. 7A is a perspective view of a plurality of scaffolds having channels, prior to placement of the plurality of channels in a stacked orientation as described herein. FIG. 7B is a perspective view of a composite formed from the plurality of scaffolds of FIG. 7A.

Figure 9:
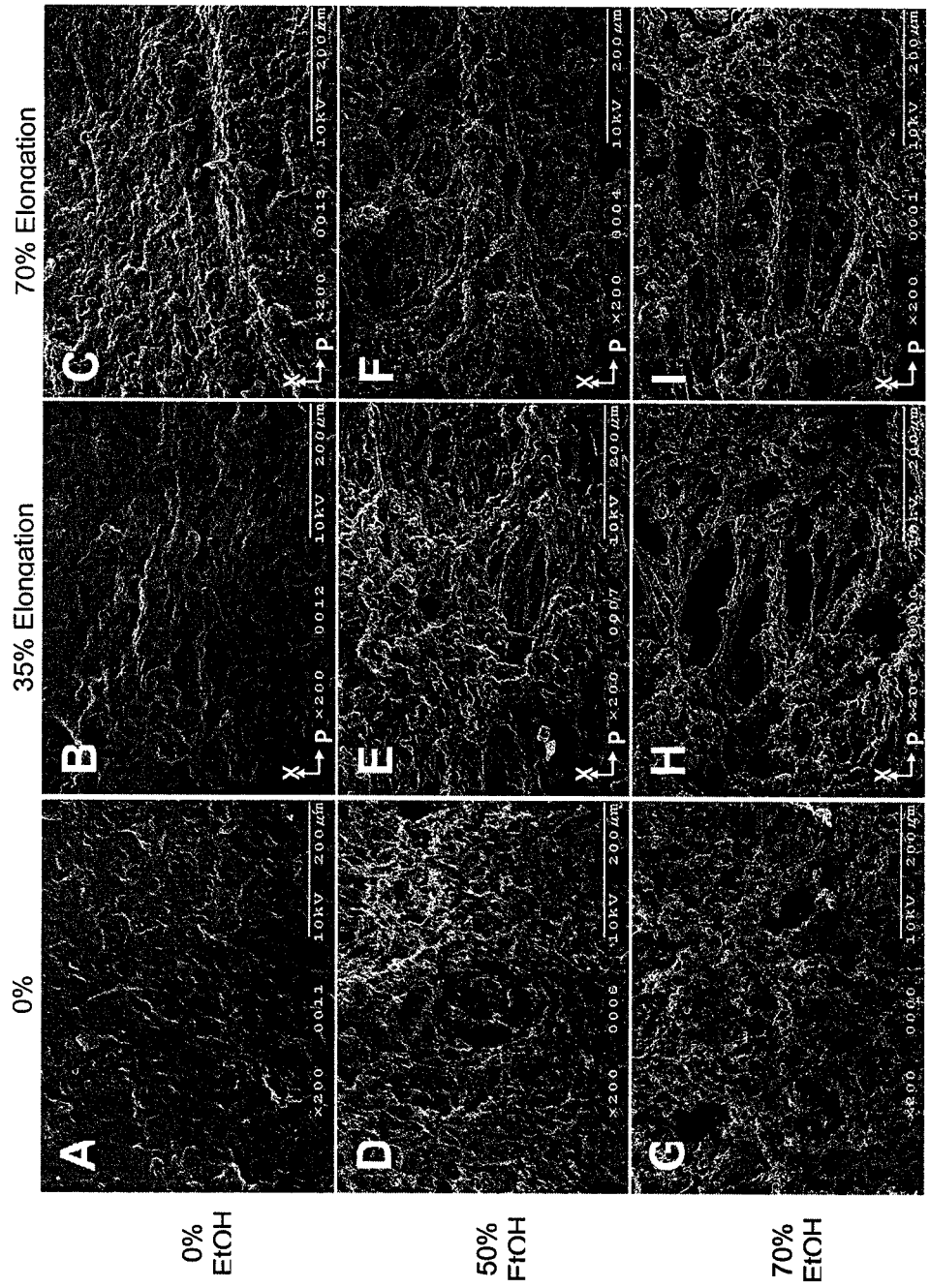

FIG. 9 displays representative scanning electron microscope (SEM) images of scaffolds that were produced as described herein. FIGS. 9A-9C display images of scaffolds made with 0% EtOH nonsolvent. FIGS. 9D-9F display images of scaffolds made with 50% EtOH nonsolvent. FIGS. 9G-9I display images of scaffolds made with 70% EtOH nonsolvent. The scaffolds displayed in FIGS. 9A, 9D, and 9G were not elongated. The scaffolds displayed in FIGS. 9B, 9E, and 9H were elongated 35%. The scaffolds displayed in FIGS. 9C, 9F, and 9I were elongated 70%. Scale bars are 200 μm.

Figure 10:
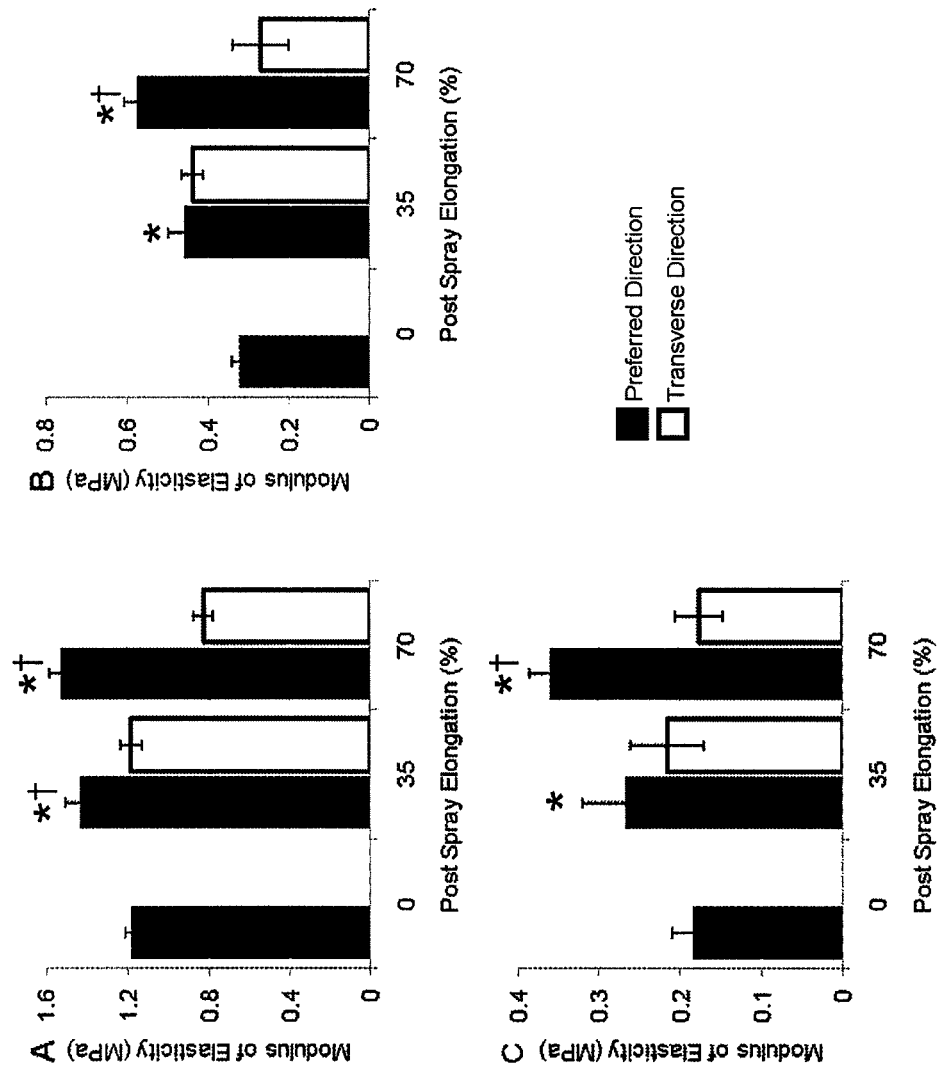

FIG. 10 displays the effective moduli of elasticity for various scaffolds produced as described herein. The modulus of elasticity of scaffolds fabricated with 0% EtOH, 50% EtOH, and 70% EtOH are displayed in FIGS. 10A, 10B, and 10C, respectively. Longitudinal moduli were compared to 0% elongation (*). 35% and 70% elongated scaffolds were compared to themselves in the longitudinal and transverse directions (†).

Figure 11:
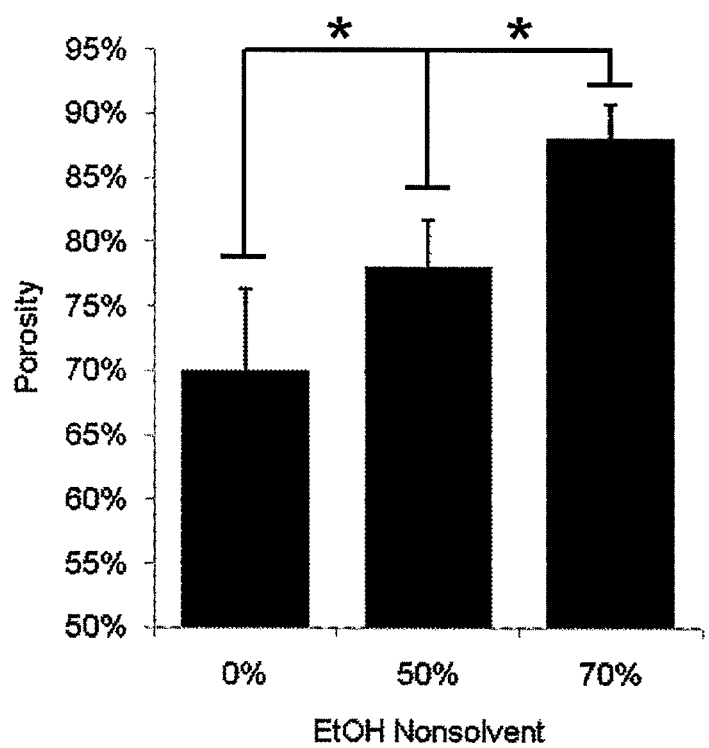

FIG. 11 displays the porosity of scaffolds fabricated with varying nonsolvent concentrations of EtOH as described herein. (n=12 for 0% EtOH concentrations, n=7 for 50% and 70% EtOH concentrations).

Figure 12A:
Figure 12B:
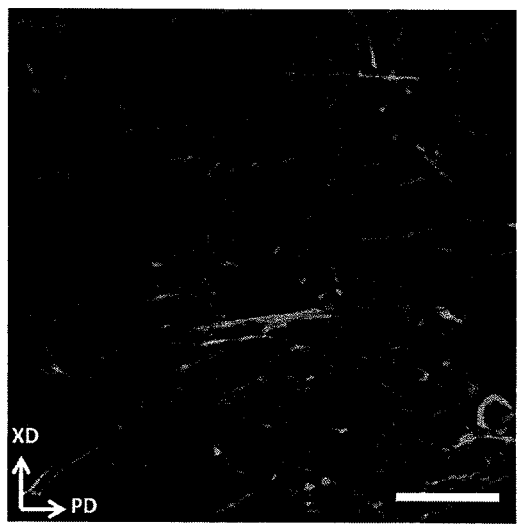

FIG. 12A is a confocal image of aligned fibroblasts in a scaffold that was produced as described herein but that was not subjected to elongation. FIG. 12B is a confocal image of aligned fibroblasts in a scaffold that was elongated by 70% as described herein. The preferred direction (PD) and transverse direction (XD) of the scaffold are indicated. Scale bar 20 µm.

Figure 13A:
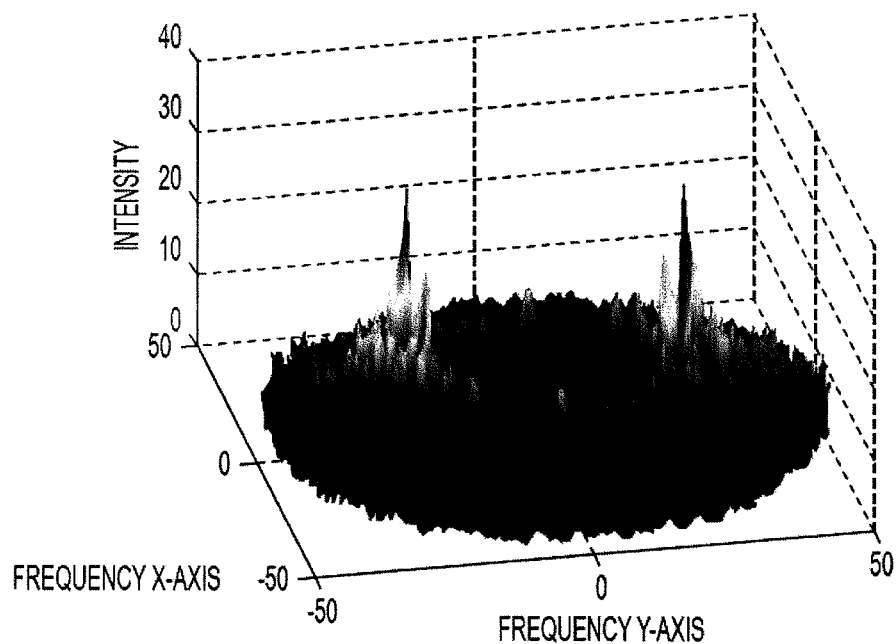
Figure 13B:
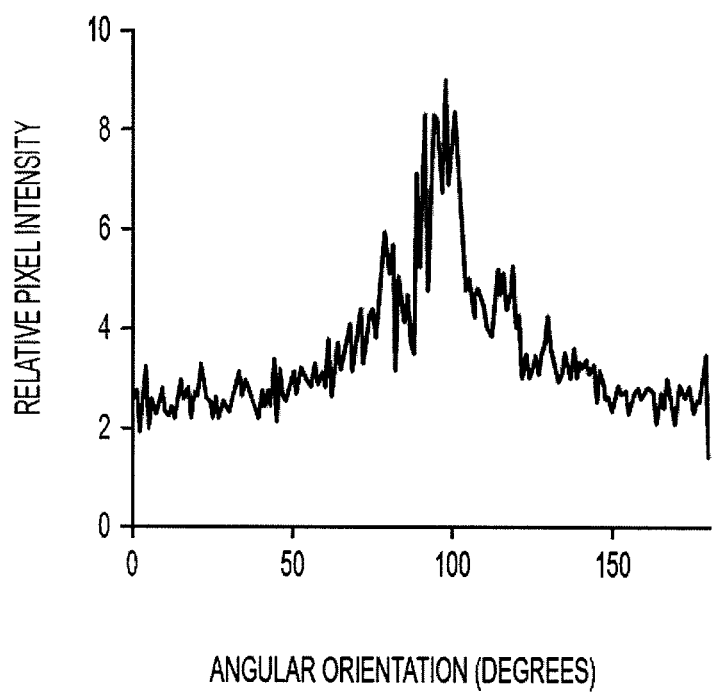

FIG. 13A displays a surface plot of a 2D FFT used to calculated alignment of a scaffold produced as described herein. Frequency values outside of 20-50 were removed to decrease signal noise. FIG. 13B displays an intensity angle plot for the scaffold characterized in FIG. 13A, where the preferred direction of the scaffold was at 90°. The intensity angle plot has been shifted by 90° to align the peak with the fiber direction.

Figure 14:
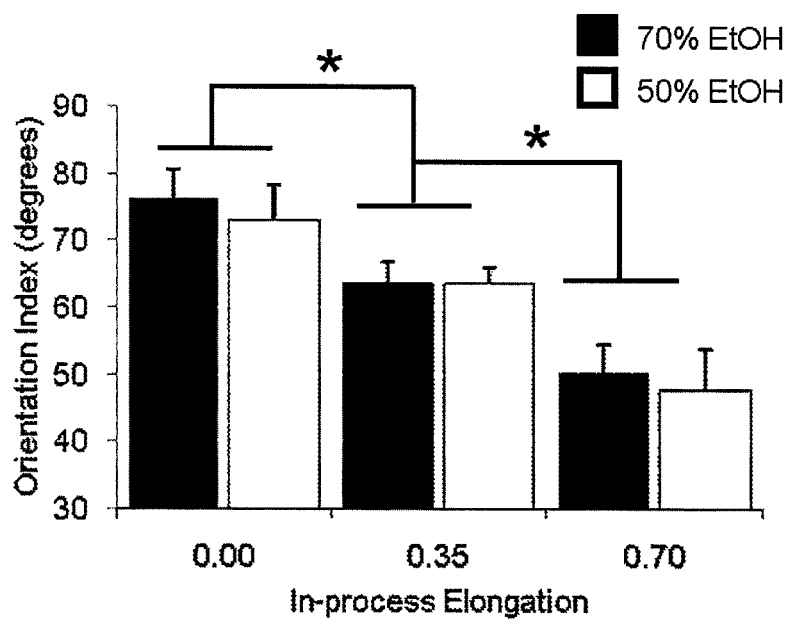

FIG. 14 displays a bar graph of the orientation indices of porous scaffolds produced as described herein.

Figure 15A:
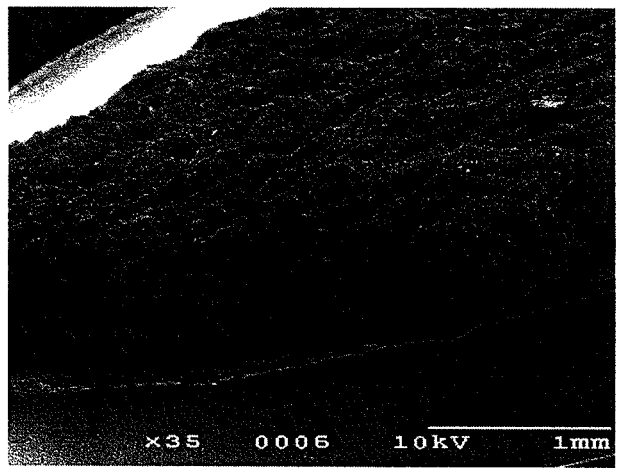

FIG. 15A displays a cross-section SEM image of a composite produced from five scaffolds fabricated with 70% EtOH non-solvent, as described herein. A close-up view of the microstructure of the composite of FIG. 15A is provided in FIG. 15B.

FIG. 16 is a table describing the effective modulus of elasticity in the preferred and transverse directions and corresponding ratios of anisotropy for various scaffolds that were produced as described herein. Values are mean±standard deviation.

DETAILED DESCRIPTION OF THE INVENTION

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to a "scaffold" can include two or more such scaffolds unless the context indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth n the claims. Except as specifically defined herein, all technical and scientific terms used herein are to be given as broad a commonly understood meaning as possible while maintaining claim validity.

As used herein, "allogeneic tissue" or "allogeneic cell" refers to a tissue or cell that is isolated from an individual and used in another individual of the same species. The term "xenogeneic tissue" or "xenogeneic cell" refers to a tissue or cell that is isolated from an individual of one species and placed in an individual of another species. The term "autogeneic tissue" or "autogeneic cell" refers to a tissue or cell that is isolated from an individual and grafted back into that same individual.

As used herein, "anisotropy" refers to the ratio of the effective modulus of elasticity of a material in a longitudinal or other preferred direction to the effective modulus of elasticity of the material in a transverse or other non-preferred direction.

As used herein, the term "biologically active agent" or "bioactive agent" means an agent that is capable of providing a local or systemic biological, physiological, or therapeutic effect in the biological system to which it is applied.

As used herein, the term "cellular alignment" means the measurement of the alignment of cellular components, such as actin filaments. The "cellular alignment" of a material is expressed as the smallest angle that encompasses the angular direction of 50% of the fibers of the material. Accordingly, a small angle indicates that most of the fibers are oriented in the same direction (highly aligned), while a large angle indicates that the fibers are exhibiting random alignment.

As used herein, the term "pharmaceutically active agent" includes a "drug" or a "therapeutic agent" and means a molecule, group of molecules, complex or substance administered to an organism for diagnostic, therapeutic, preventative medical, or veterinary purposes. This term includes externally and internally administered topical, localized and systemic human and animal pharmaceuticals, treatments, remedies, nutraceuticals, cosmeceuticals, biologicals, biomaterials, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term includes, but is not limited to, RNAi technologies and reagents, transgenes, protein growth factors, antimicrobials, antibiotics, microcidals, antiseptics, antifungals, anti-inflammatories, anesthetics, and analgesics. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA) or ribonucleic acid (RNA) as genetic materials introduced to produce a desired therapeutic effect.

As used herein, the term "polymer" refers to a relatively high molecular weight organic compound, natural or synthetic, whose structure can be represented by a repeated small unit, the monomer (e.g., polyesters, polyamides, polyvinyls, polyanhydrides, polyorthoesters, polyaminoacids, polyalkenes, polyacrylates, polyarylates, polyolefins, polyacrylamides, polysugars, polyphosphonates, polyphosphazenes, polytyrosines, polyethers, polyurethanes, polycarbonates). Synthetic polymers are typically formed by addition or condensation polymerization of monomers. Natural polymers (biopolymers) include collagens and gelatins, silks, keratins, elastins, and their recombinant polymers and peptides, and peptide-polymer combinations, nucleic acids and their derivatives, starches including cellulose derivatives, chitosans, alginates, polyhydroxyalkanoates, glycosaminoglycans, proteoglycans, fibrin glues and fibrinogen derivatives for this purpose.

As used herein, the term "copolymer" refers to a polymer formed from two or more different repeating units (monomer residues, such as PLA-PLGA glycolide-lactide copolymers). By way of example and without limitation, a copolymer can be an alternating copolymer, a random copolymer, a block copolymer (e.g., Pluronics), or a graft copolymer. It is also contemplated that, in certain aspects, various block segments of a block copolymer can themselves comprise copolymers. These blocks can impart specific chemical and physical properties important to their use herein, such as depot forming properties in tissues as rate-limiting release barriers, control of polymer degradation, solubilization of drugs, and control of drug-particle encapsulate size (micro and nano encapsulates).

The term "pharmaceutically acceptable" describes a material that is not biologically or otherwise undesirable, i.e., without causing an unacceptable level of undesirable biological effects or interacting in a deleterious manner, and which allows both formulation and delivery of biologically active and pharmaceutically active agents to produce a desired therapy without clinically unacceptable effects.

As used herein, "porosity" refers to the ratio of the volume of the void space of a solid material to the total volume of the solid material.

As used herein, "simultaneous" and "simultaneously" refer to any two or more actions that exist or occur at substantially the same time. However, as used herein, two actions can occur "simultaneously" even though they are not exactly coincident. For example, two actions can occur "simultaneously" even though the first action starts before the second action starts and the section action continues after the first action ends.

As used herein, "transgenic" refers to an organism in which DNA has been artificially introduced, or a compound that is produced in the organism encoded by the DNA that has been artificially introduced. The transgenic compound can be the DNA itself, RNA transcribed from the DNA, a protein that has been translated from the DNA, or combinations thereof.

Disclosed herein are systems and methods for producing scaffolds. Also disclosed are composites comprising a plurality of scaffolds. In one aspect, a system for producing at least one scaffold can comprise a polymer solution and a non-solvent. In one aspect, the polymer solution can comprise polyether polyurethane. In this aspect, the polymer solution can comprise a desired amount of polyether polyurethane. It is contemplated that the desired amount of polyether polyurethane can range from about 1% to about 10% by weight of the polymer solution, more preferably from about 2% to about 6% by weight of the polymer solution. Optionally, in an additional aspect, the polymer solution can further comprise dimethylacetamide. In this aspect, it is contemplated that the polyether polyurethane can be dissolved therein the dimethylacetamide. In another aspect, the polymer solution can comprise a desired amount of polycaprolactone. In this aspect, the desired amount of polycaprolactone can range from about 1% to about 10% by weight of the polymer solution, more preferably from about 2% to about 6% by weight of the polymer solution. Optionally, the polymer solution can further comprise acetone. It is contemplated that the polycaprolactone can be dissolved therein the acetone. In yet another aspect, the polymer solution can comprise a desired amount of collagen gel. In this aspect, the desired amount of collagen gel can range from about 1% to about 10% by weight of the polymer solution, more preferably from about 2% to about 6% by weight of the polymer solution. Optionally, the polymer solution can further comprise water. It is contemplated that the collagen gel can be dissolved therein the water. In still a further aspect, the polymer solution can comprise a desired amount of at least one of polyacrylonitrile, polyvinyl chloride, and polysulfone. In this aspect, the desired amount of at least one of polyacrylonitrile, polyvinyl chloride, and polysulfone can range from about 0.1% to about 10% by weight of the polymer solution, more preferably from about 0.5% to about 6% by weight of the polymer solution. Optionally, the polymer solution can further comprise dimethylacetamide. It is contemplated that the at least one of polyacrylonitrile, polyvinyl chloride, and polysulfone can be dissolved therein the dimethylacetamide.

In a further aspect, the non-solvent can comprise deionized water. In this aspect, the non-solvent can further comprise a desired amount of ethanol (EtOH). It is contemplated that the desired amount of ethanol can range from about 0% to about 100% by weight of the non-solvent depending on the desired porosity of the scaffold. It is further contemplated that the at least one scaffold can be biocompatible. It is still further contemplated that the at least one scaffold can be biosynthetic.

In another aspect, and with reference to FIGS. 1-5B, the system 10 for producing the at least one scaffold 12 can comprise a backing member 14. In this aspect, the backing member 14 can comprise at least one of aluminum and silicone. However, it is contemplated that the backing member 14 can comprise any other conventional materials having a relatively low affinity for the materials used to produce the at least one scaffold 12, including, for example and without limitation, conventional polyolefins such as polyethylene and polypropylene, and conventional fluoropolymers such as polytetrafluoroethylene. In an additional aspect, the system 10 for producing the at least one scaffold 12 can comprise at least one support element 15 secured thereon the backing member 14. In this aspect, each support element 15 can have a receiving portion 18 configured to promote adherence of a scaffold 12 of the at least one scaffold. It is contemplated that each support element 15 can comprise materials having a relatively higher affinity for the materials from which the at least one scaffold 12 is made than the backing member. In a further aspect, the backing member 14 can be positioned within a spray chamber.

In one aspect, the at least one support element 15 can optionally comprise at least one frame 16 as depicted in FIGS. 2A-4C. In an additional aspect, the receiving portion 18 of each frame 16 of the at least one frame can comprise a central opening 19 defined by an inner portion of each frame. It is contemplated that at least a portion of each frame 16 of the at least one frame can be configured to promote adherence of a scaffold 12. In another aspect, each frame 16 of the at least one frame can comprise at least one of aluminum and polyester. However, it is contemplated that each frame 16 of the at least one frame can comprise other conventional materials, including, for example and without limitation, thin polyester films, stiff polyurethanes, nylons and nylon copolymers. In this aspect, it is contemplated that each frame 16 can be coated with silicone to prevent the scaffolds 12 from sticking to the frame. It is further contemplated that the frames 16 of the at least one frame can be disposable.

In an additional aspect, each frame 16 of the at least one frame can have an outer length, an outer width, and a thickness. In this aspect, it is contemplated that the thickness of each frame 16 of the at least one frame can range from about 0.10 cm to about 2.00 cm. It is further contemplated that the outer length of each frame 16 of the at least one frame can range from about 0.50 cm to about 25 cm. It is still further contemplated that the outer width of each frame 16 of the at least one frame can range from about 0.50 cm to about 25 cm. In a further aspect, the central opening 19 of each frame 16 of the at least one frame can have a length and a width. In this aspect, it is contemplated that the length of each central opening 19 can range from about 0.40 cm to about 20 cm. It is further contemplated that the width of each central opening 19 can range from about 0.40 cm to about 20 cm. In one aspect, the ratio of the length of the central opening to the width of the central opening can be greater than or equal to one. As one skilled in the art will appreciate, the relative dimensions described above are meant to be exemplary and as such are not meant to be limiting.

In another aspect, it is contemplated that the at least one frame 16 can be configured to permit elongation of each scaffold 12 of the at least one scaffold by a desired length such that each scaffold develops at least one desired property. It is contemplated that the desired length of elongation can correspond to a particular desired property. In a further aspect, the at least one desired property can comprise at least one of, for example and without limitation, desired anisotropic properties, a desired cellular alignment, and a desired porosity. In this aspect, it is contemplated that the desired anisotropic properties can correspond to an anisotropy ranging from about 1.00 to about 3.00. It is further contemplated that the desired porosity can range from about 0.50 to about 0.99. It is still further contemplated that the desired cellular alignment can correspond to an orientation index ranging from between about 30 degrees to about 90 degrees.

It is still further contemplated that both the elongation of each scaffold and the non-solvent concentration used to produce each scaffold can contribute to the development of the at least one desired property in each scaffold. For example, and without limitation, the desired porosity of a scaffold can be obtained by selectively adjusting the non-solvent concentration used to produce the scaffold, and the desired anisotropic properties and desired cellular alignment of a scaffold can be obtained by selectively adjusting the elongation of the scaffold.

In a further aspect, at least one of a first and a second portion 20, 21 of each frame 16 can be selectively moveable such that each scaffold 12 is elongated by the desired length along a longitudinal axis L of the frame. In this aspect, at least one of the first and the second portion 20, 21 of each frame 16 can optionally be selectively moved along a first and a second elongation guide member 22, 23 of the frame. It is contemplated that the first and second elongation guide members 22, 23 of each frame 16 can be substantially parallel to the longitudinal axis L of each frame. In another aspect, the first and second portions 20, 21 of each frame can each comprise a first side member 24 and a second side member 25. In this aspect, it is contemplated that the first and second portions 20, 21 of each frame 16 can be positioned in opposed relation to one another along the longitudinal axis L of the frame. It is further contemplated that the first and second portions 20, 21 of each frame 16 can be positioned in opposed relation to one another so as to define at least a portion of the central opening 19.

In an additional aspect, it is contemplated that the first elongation guide member 22 can be attached thereto the first side members 24 of the first and second portions 20, 21 of each frame 16. It is further contemplated that the second elongation guide member 23 can be attached thereto the second side members 25 of the first and second portions 20, 21 of each frame 16. In one aspect, the first and second elongation guide members 22, 23 can be attached to the frames 16 using ultraviolet cure adhesive.

In another aspect, it is contemplated that the first and second elongation guide members 22, 23 can constrain the elongation of the scaffolds 12 thereon each frame to a maximum elongated length. In this aspect, the first and second elongation guide members 22, 23 can constrain the maximum elongated length of each scaffold 12 to less than about 6.00 cm. However, it is contemplated that the maximum elongated length can be any selected length. It is further contemplated that the maximum elongated length can correspond to a selected percentage of elongation of each scaffold 12, including, for example and without limitation, 20%, 30%, 40%, 50%, 60%, 70%, 80%, and 90% relative to a non-elongated length of each scaffold.

Figure 3:
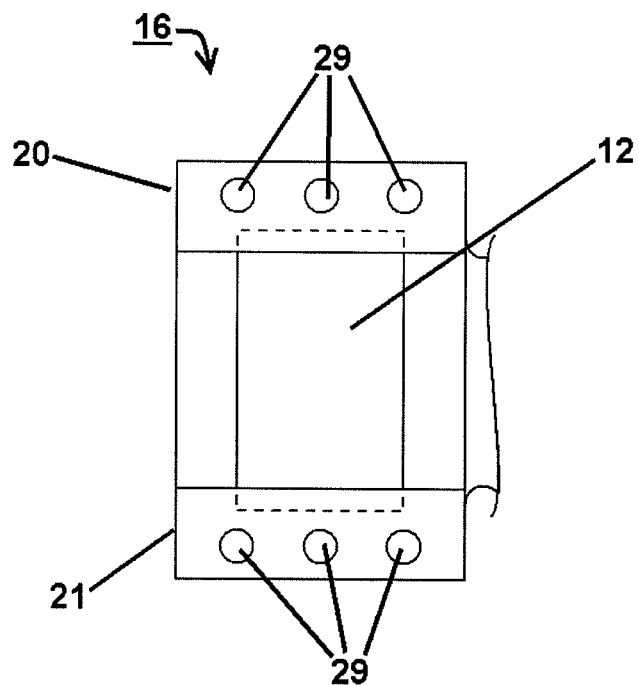
Figure 4A:
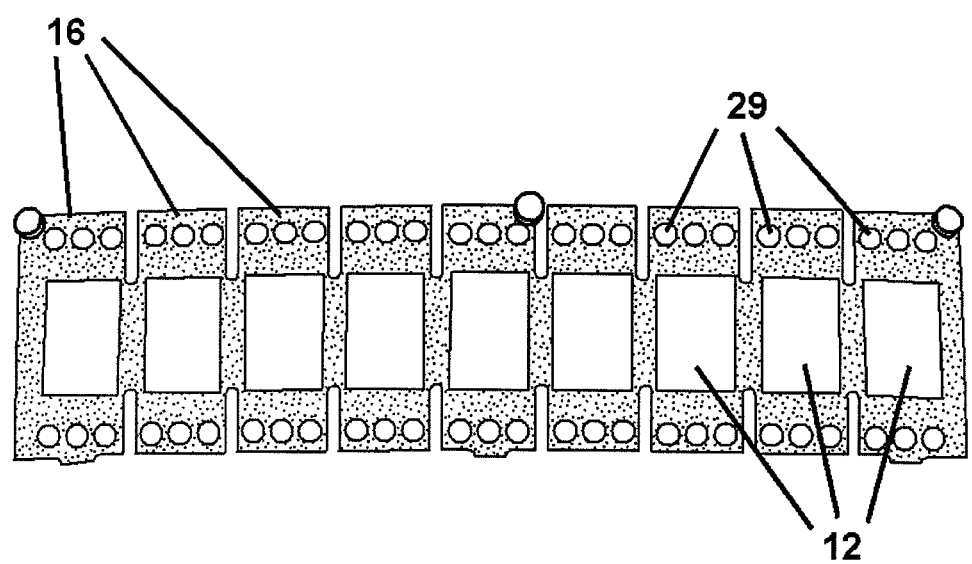
Figure 4B:
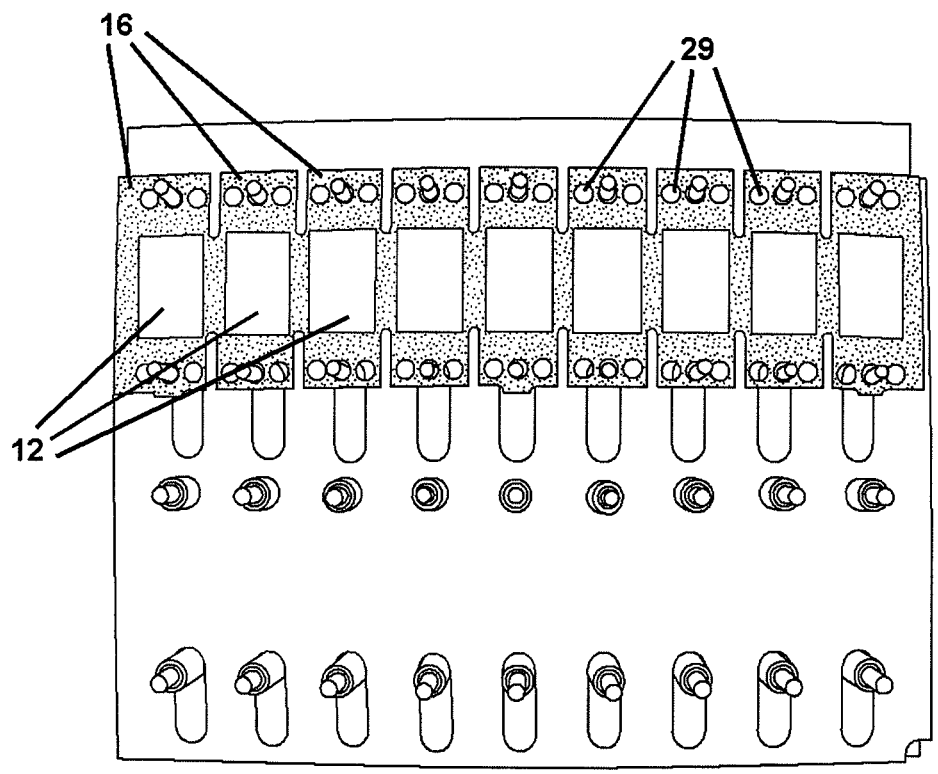
Figure 4C:
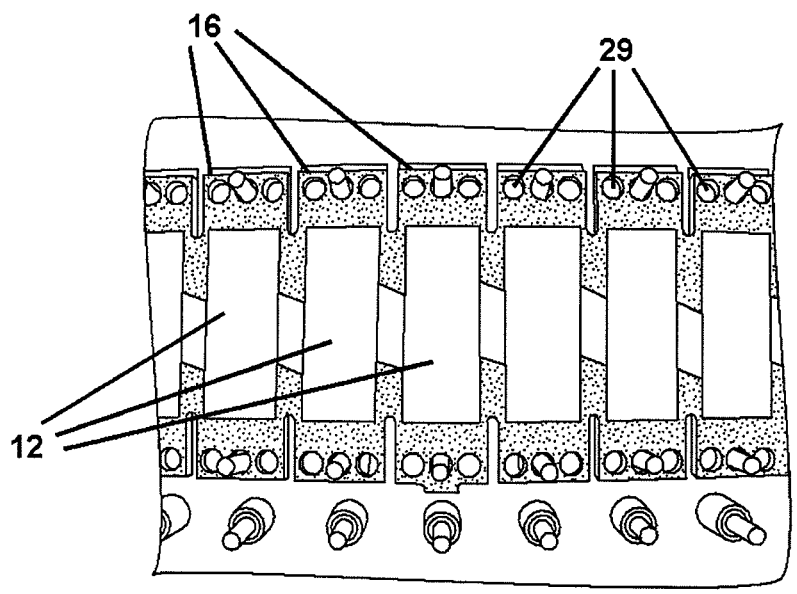

In a further aspect, and with reference to FIGS. 3-4C, at least one of the first portion 20 and the second portion 21 of each frame 16 of the at least one frame can comprise at least one bore 29 defined therein the first portion or the second portion of the frame. In this aspect, the at least one bore 29 can be configured to receive a pin, rod, nail, screw, or other elongate member by which each frame 16 can be held or stabilized by a stationary object as depicted in FIG. 4B. It is contemplated that following receipt of the elongate member therein a bore 29 of a frame 16, the elongate member can be used to guide the elongation of a scaffold 12 therein the frame along the longitudinal axis L of the frame as depicted in FIG. 4C.

In an additional aspect, the first and second portions 20, 21 of each frame can further comprise a base member 26. In this aspect, the first side member 24, the base member 26, and the second side member 25 of the first portion 20 of each frame 16 can cooperate to form a U-shape, thereby defining at least a portion of the central opening 19 of the frame 16. Similarly, it is contemplated that the first side member 24, the base member 26, and the second side member 25 of the second portion 21 of each frame 16 can cooperate to form a U-shape, thereby defining at least a portion of the central opening 19 of the frame 16.

In still another aspect, each frame 16 of the at least one frame can further comprise first and second screens 27a, 27b. In this aspect, the first screen 27a of each frame 16 can be secured thereto the base member 26 of the first portion 20 of the frame, and the second screen 27b of the frame can be secured thereto the base member of the second portion 21 of the frame. It is contemplated that the first screen 27a can be secured thereto the base member 26 of the first portion 20 of the frame 16 such that at least a portion of the first screen extends into the central opening 19 of the frame. Similarly, it is contemplated that the second screen 27b can be secured thereto the base member 26 of the second portion 21 of the frame 16 such that at least a portion of the second screen extends into the central opening 19 of the frame. In a further aspect, the first and second screens 27a, 27b of each frame 16 can comprise porous, stainless steel screens. In another aspect, the first and second screens 27a, 27b of each frame 16 can be configured to promote adherence of a scaffold 12 as described herein.

In an additional aspect, the at least one frame 16 can comprise a plurality of frames. In this aspect, it is contemplated that the plurality of frames 16 can be arranged as an array of frames as depicted in FIGS. 4A-4C. It is further contemplated that at least some frames 16 within the array of frames can be connected to adjacent frames within the array. It is still further contemplated that the first and second portions 20, 21 of the frames 16 within the array of frames can be configured to collectively move in a selected manner so as to uniformly elongate the scaffolds 12 therein each frame by the desired length, as shown in FIG. 4C.

Figure 5A:
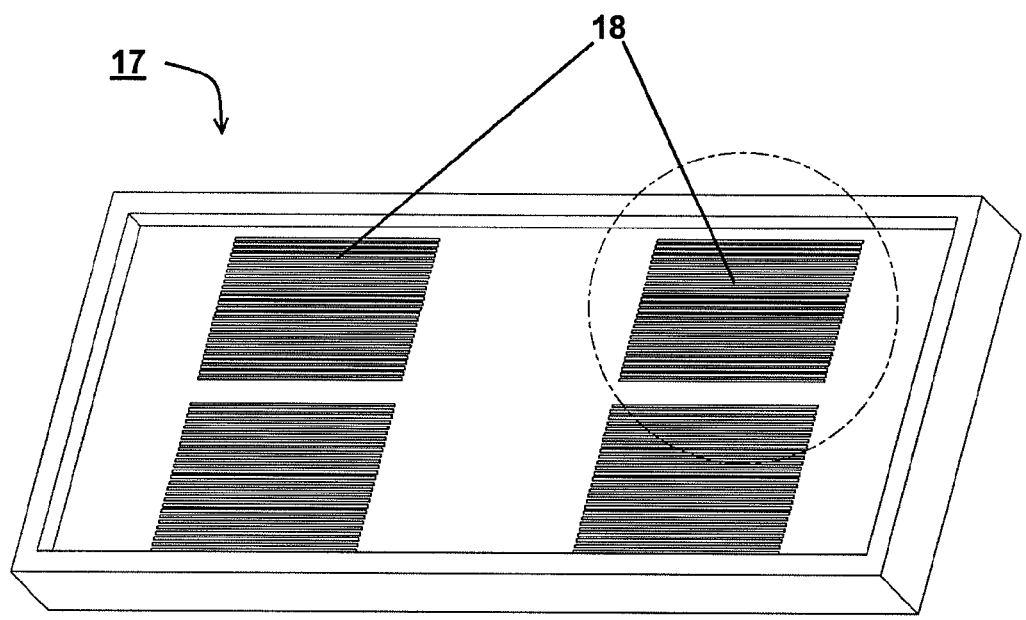
FIG. 5A is a perspective view of a mold for receiving scaffolds, as described herein.
Figure 5B:
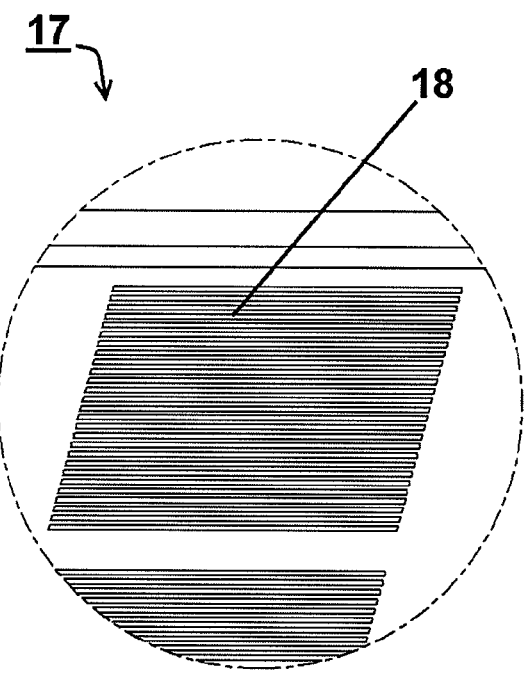
FIG. 5B is a close-up perspective view of a receiving portion of the mold of FIG. 5A.
Figure 8A:
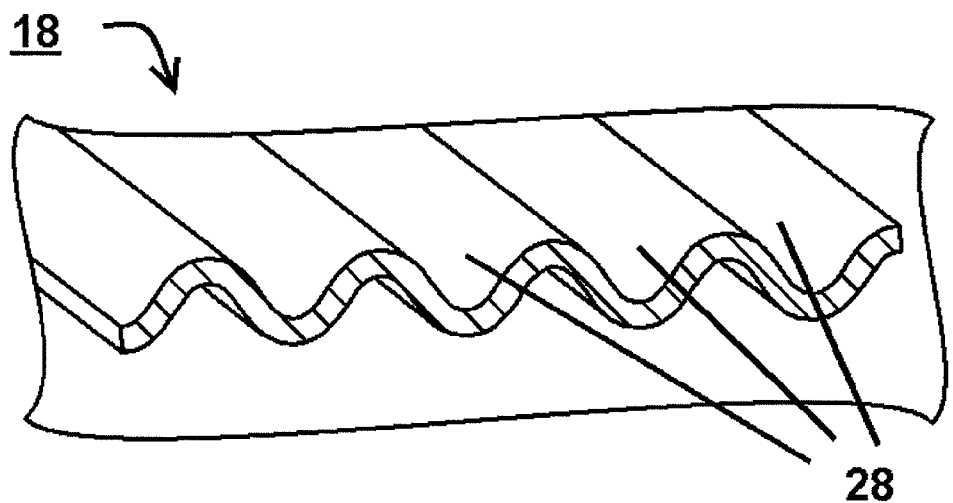
FIG. 8A is a perspective view of a scaffold having channels, as described herein.
Figure 8B:
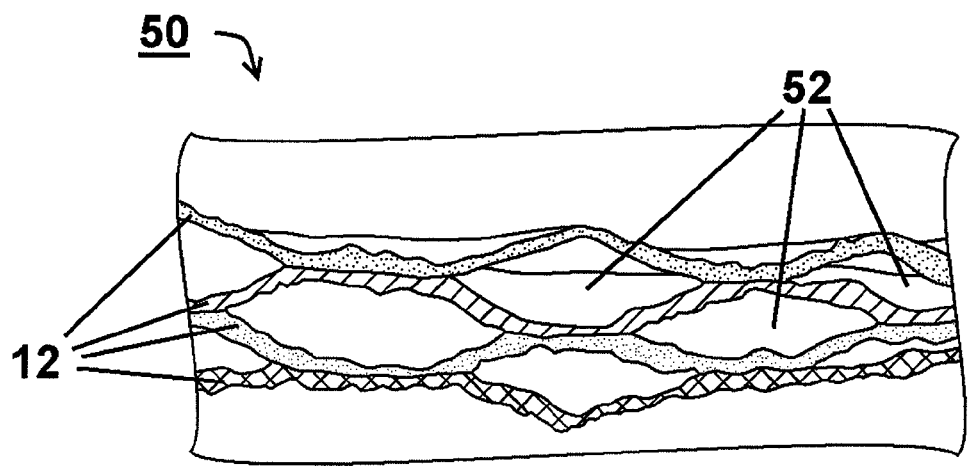
FIG. 8B is a perspective view of a composite having perfusion channels formed from the channels of a plurality of scaffolds as depicted in FIG. 8A.

In a further aspect, and with reference to FIGS. 5A-5B, the at least one support element 15 can optionally comprise at least one mold 17. In an another aspect, the receiving portion 18 of the at least one mold 17 can comprise a corrugated outer surface. In this aspect, it is contemplated that the corrugated outer surface of each mold 17 of the at least one mold can comprise at least one of polydimethylsiloxane, silicone, conventional metals such as aluminum and stainless steel, conventional fluoropolymers such as polytetrafluoroethylene, and conventional polyolefins such as polyethylene and polypropylene. It is further contemplated that the mold can have a plurality of receiving portions as depicted in FIG. 5A. In an additional aspect, and with reference to FIGS. 7A and 8A, the corrugated outer surface of each mold 17 of the at least one mold can be configured to define a plurality of channels 28 therein a scaffold 12 of the at least one scaffold. It is contemplated that the plurality of channels 28 defined therein each scaffold 12 can have at least one desired property. In another aspect, the at least one desired property of the plurality of channels 28 defined therein each scaffold 12 can comprise at least one of a desired width, a desired depth, and a desired spacing of channels. In this aspect, it is contemplated that the desired width of the plurality of channels 28 defined therein each scaffold 12 can range from about 50 µm to about 1,000 µm. It is further contemplated that the desired depth of the plurality of channels 28 defined therein each scaffold 12 can range from about 50 µm to about 750 µm. It is still further contemplated that the desired spacing of the channels can range from about 50 to about 500 µm.

In an additional aspect, the system 10 for producing the at least one scaffold 12 can comprise means for simultaneously spraying a polymer solution and a non-solvent therein one or more receiving portions 18 of the at least one support element 15. In this aspect, it is contemplated that a scaffold 12 of the at least one scaffold can be formed therein and adhered to each support element 15. In an additional aspect, it is contemplated that the means for simultaneously spraying a polymer solution and a non-solvent can be configured to simultaneously spray the polymer solution and the non-solvent at respective, desired spray rates. In this aspect, it is contemplated that the desired spray rate of the polymer solution can range from about 3.0 grams per minute to about 8.5 grams per minute. It is further contemplated that the desired spray rate of the non-solvent can range from about 5.0 grams per minute to about 55.0 grams per minute.

In a further aspect, the means for simultaneously spraying the polymer solution and the non-solvent can comprise a spraying machine 30. In one aspect, the spraying machine 30 can comprise a processor 32. In another aspect, the spraying machine 30 can comprise a motor 34 in electrical communication with the processor 32. In an additional aspect, the spraying machine 30 can comprise a spindle head 36 coupled to the motor 34 and in electrical communication with the processor 32. In this aspect, the spindle head 36 can be configured for selective three-dimensional movement. In a further aspect, the spraying machine 30 can comprise at least one spindle attached thereto and extending therefrom the spindle head 36.

In another aspect, the spraying machine 30 can comprise at least two fluid reservoirs 38. In this aspect, it is contemplated that a first fluid reservoir of the at least two fluid reservoirs 38 can contain the polymer solution. It is further contemplated that a second fluid reservoir of the at least two fluid reservoirs 38 can contain the non-solvent. In an additional aspect, the spraying machine 30 can comprise at least two spray nozzles 40 coupled to the spindle head 36. In this aspect, a first spray nozzle of the at least two spray nozzles can be in fluid communication with a first fluid reservoir of the at least two fluid reservoirs 38, including, for example, the first fluid reservoir. It is further contemplated that a second spray nozzle of the at least two spray nozzles 40 can be in fluid communication with a second fluid reservoir of the at least two fluid reservoirs 38, including, for example, the second fluid reservoir. It is still further contemplated that each spray nozzle 40 of the at least two spray nozzles can be configured to spray fluid. In one aspect, each spray nozzle 40 of the at least two spray nozzles can be coupled to a spindle of the at least one spindle of the spindle head 36. In another aspect, each spray nozzle 40 of the at least two spray nozzles can be configured to spray fluid at a spray speed ranging from about 0.50 cm/s to about 1.50 cm/s. In an additional aspect, the at least two spray nozzles 40 can be spaced from the at least one support element 15 thereon the backing member 14 by a predetermined distance ranging from about 10 cm to about 30 cm.

In a further aspect, the processor 32 of the spraying machine 30 can be configured to perform the step of activating the first and second spray nozzles 40 to spray the polymer solution and the non-solvent at their respective, desired spray rates. In an additional aspect, the processor 32 of the spraying machine 30 can be configured to perform the step of selectively controlling the three-dimensional movement of the spindle head 36 such that the polymer solution and the non-solvent are sprayed in a desired pattern. In this aspect, the desired pattern can be a serpentine pattern. However, it is contemplated that the desired pattern can be any pattern that can be sprayed within the receiving portions 18 of the at least one support element 15.

In still another aspect, the spraying machine 30 can further comprise a pressure regulator 42 in fluid communication with the at least two spray nozzles 40 and in electrical communication with the processor 32. In this aspect, the pressure regulator 42 can be configured to selectively control the pressure at which fluid is sprayed from the at least two spray nozzles 40. It is further contemplated that the processor 32 can be configured to selectively control the pressures at which the polymer solution and the non-solvent are sprayed from the first and second spray nozzles 40.

In yet an additional aspect, the spraying machine 30 can comprise an interface device by which a user can communicate with the processor 32. For example, and without limitation, the interface device can comprise any conventional electrical communications device, including, for example and without limitation, a computer, keypad, touchscreen display, memory, voice-activation device, remote control, and the like.

In one aspect, the system for producing the at least one scaffold can further comprise means for rinsing the at least one scaffold. In this aspect, it is contemplated that the means for rinsing the at least one scaffold can rinse the at least one scaffold after each scaffold is formed therein and adhered to a support element.

In another aspect, the system for producing the at least one scaffold can further comprise means for drying the at least one scaffold. In this aspect, it is contemplated that means for drying the at least one scaffold can dry the at least one scaffold after each scaffold is elongated by the desired length.

In use, the systems described herein can be employed in methods for producing at least one scaffold. In one aspect, a method for producing at least one scaffold can comprise securing at least one support element thereon a backing member as described herein. In another aspect, the method for producing at least one scaffold can comprise simultaneously spraying a polymer solution and a non-solvent therein one or more receiving portions of the at least one support element such that a scaffold of the at least one scaffold is formed therein and adhered to each support element. However, in some aspects, the method for producing at least one scaffold can comprise about simultaneously spraying a polymer solution and a non-solvent therein one or more receiving portions of the at least one support element such that a scaffold of the at least one scaffold is formed therein and adhered to each support element. It is further contemplated that the polymer solution can be sprayed individually onto a non-solvent surface. Optionally, in an additional aspect, the method for producing the at least one scaffold can comprise elongating each scaffold of the at least one scaffold by a desired length as described herein. In this aspect, it is contemplated that each scaffold can be elongated such that each scaffold develops at least one desired property as described herein.

In one aspect, the method for producing the at least one scaffold can further comprise rinsing the at least one scaffold after the step of simultaneously spraying a polymer solution and a non-solvent. In this aspect, the step of rinsing the at least one scaffold can occur prior to the step of elongating each scaffold of the at least one scaffold. Alternatively, the step of rinsing the at least one scaffold can occur after the step of elongating each scaffold of the at least one scaffold. In an additional aspect, the method for producing the at least one scaffold can further comprise drying the at least one scaffold after the step of elongating each scaffold.

In another aspect, the step of simultaneously spraying the polymer solution and the non-solvent can comprise simultaneously spraying the polymer solution and the non-solvent at respective, desired spray rates as described herein.

In an additional aspect, the step of securing at least one support element thereon a backing member can comprise securing at least one frame as described herein thereon a backing member. In a further aspect, the step of simultaneously spraying a polymer solution and a non-solvent therein one or more receiving portions can comprise simultaneously spraying a polymer solution and a non-solvent therein one or more central openings of the at least one frame as described herein. In this aspect, the step of elongating each scaffold can comprise selectively moving at least one of the first and the second portion of each frame such that each scaffold is elongated by the desired length along the longitudinal axis of the frame as described herein. In this aspect, the step of elongating each scaffold can comprise selectively moving at least one of the first and the second portion of each frame along the first and the second elongation guide members of the frame.

In a further aspect, and with reference to FIGS. 6A-6B, a method for producing a composite 50 comprising a plurality of scaffolds 12 is disclosed. In this aspect, the method for producing a composite comprises the steps of securing at least one support element thereon a backing member and simultaneously spraying a polymer solution and a non-solvent therein one or more receiving portions of the at least support element, as described herein. In another aspect, the method for producing a composite comprises positioning the plurality of scaffolds 12 in a stacked relationship such that at least one scaffold is superposed relative to another scaffold. In a further aspect, the method for producing a composite comprises curing the plurality of scaffolds 12 such that the scaffolds are connected together to form the composite 50. In this aspect, it is contemplated that the plurality of scaffolds 12 can comprise two or more scaffolds. However, it is contemplated that any number of scaffolds 12 can be used to form the composite 50.

In one aspect, the step of positioning the plurality of scaffolds in a stacked relationship can further comprise positioning a plurality of spaced tubular members having a selected diameter therebetween contiguous scaffolds. In this aspect, it is contemplated that the method for producing a composite can further comprise removing the plurality of spaced tubular members from the composite to thereby form a plurality of channels therein the composite. In an additional aspect, the selected diameter of the plurality of spaced tubular members can range from about 200 µm to about 1,000 µm. In a further aspect, the plurality of spaced tubular members can comprise at least one of polytetrafluoroethylene, steel, aluminum, silicone, Teflon, and other conventional non-adhesive polymers.

In another aspect, the method for producing a composite can optionally comprise elongating at least one scaffold of the plurality of scaffolds by a desired length such that each elongated scaffold develops at least one desired property as described herein prior to the step of positioning the plurality of scaffolds in a stacked relationship.

In one aspect, the step of securing at least one support element thereon a backing member can comprise securing at least one mold as described herein thereon the backing member. In this aspect, it is contemplated that the corrugated outer surface of each mold of the at least one mold can define a plurality of channels 28 therein a scaffold 12 of the plurality of scaffolds, as depicted in FIGS. 7A-8B. It is further contemplated that the plurality of channels defined therein each scaffold can have at least one desired property as described herein.

In another aspect, the plurality of channels 28 defined therein each scaffold 12 can cooperate with the plurality of channels defined therein contiguous scaffolds to form perfusion channels 52 extending therethrough the composite 50. However, it is contemplated that the plurality of channels defined therein a scaffold can also function as perfusion channels when the scaffold is contiguous with flat scaffolds or other scaffolds that do not have a plurality of channels defined therein, including, for example and without limitation, the scaffolds formed therein the frames as described herein.

In an additional aspect, and with reference to FIGS. 6A-8B, a composite 50 having a longitudinal axis C is disclosed. In one aspect, the composite 50 can comprise a plurality of scaffolds 12 connected to one another in a stacked relationship such that at least one scaffold is superposed relative to another scaffold. Optionally, in this aspect, the plurality of scaffolds 12 can be connected to one another in a stacked relationship as described herein. It is contemplated that each scaffold 12 of the plurality of scaffolds can possess at least one desired property as described herein, including, for example and without limitation, desired anisotropic properties, a desired cellular alignment, a desired porosity, desired perfusion properties, and desired mechanical properties, such as durometer and molecular weight. In another aspect, it is contemplated that each scaffold 12 of the plurality of scaffolds can comprise selected biologically active materials, such as, for example and without limitation, growth factors and ligands. In still another aspect, it is contemplated that each scaffold 12 of the plurality of scaffolds can comprise biological matrix materials, such as, for example and without limitation, collagen, elastin, and fibronectin. It is contemplated that the properties of the scaffolds 12 of the plurality of scaffolds can function in a complementary manner within the composite 50 to produce a desired result.

In a further aspect, the composite 50 comprises a plurality of spaced perfusion channels 52 positioned therebetween contiguous scaffolds therein the composite. In this aspect, it is contemplated that the plurality of spaced perfusion channels 52 can extend substantially parallel to the longitudinal axis C of the composite 50.

Also disclosed are scaffolds comprising one or more bioactive agents or pharmaceutically active agents. For example, disclosed are scaffolds comprising a biocompatible, porous substrate; a degradable polymer coated on the substrate surface; and one or more bioactive agents or pharmaceutically active agents encapsulated by polymer, wherein the polymer has a structure and a molecular weight selected to biodegrade over a time period when implanted within a subject and thereby release the agent over the time period.

Disclosed herein are scaffolds comprising one or more agents, including bioactive agents, pharmaceutically active agents, or combinations thereof. The disclosed scaffolds can in some aspects release one or more agents at the scaffold implantation site. In some aspects, the agent release is a controlled, extended release. Thus, also disclosed are methods of making the disclosed scaffolds to select the rate of controlled release of bioactive agents, pharmaceutically active agents, or combinations thereof to produce therapy at the implant site.

The scaffolds disclosed herein can be combination biomaterials of one or more agents and one or more substrates suitable for use as scaffolds. The one or more biomaterial substrates can generally be selected based on the target tissue and the intended biomaterial use.

By "encapsulated" is meant that the agent(s) can be either incorporated into the polymer or into or onto the substrate and covered by the polymer coating, such that release of the agent(s) from the scaffolds is hindered and controlled by the polymer coating barrier and its degradation at the site of application. Also as disclosed herein, one or more agent(s) can be further encapsulated within microspheres or nanospheres or particles prior to loading onto scaffold or into the polymer coating. Thus, the agent(s) can be both (1) microencapsulated by microspheres, nanospheres, or other agent-particle formulations, and (2) macro-encapsulated by the disclosed polymer (e.g., within or beneath the polymer coating), thus providing two tiers of loading, dosing and release control for selected agent(s).

In one aspect, the polymer can serve at least two functions in the scaffolds. First, the polymer can serve as a cohesive material that facilitates drug dosing and loading, distribution and physical and chemical compatibilization by binding, stabilizing and incorporating the biologically active and/or pharmaceutically active agent(s) to the scaffolds for eventual release. Second, the polymer can serve as a rate-controlling barrier mechanism for controlled release of the agent(s) from the polymer or from beneath the polymer after introduction into a subject. In a further aspect, the polymer chemical structure, physical structure of the coating (such as aggregation states with drugs, matrix coating crystallinity, and its domain morphology), and/or polymer molecular weight and degradation mechanisms and rates can be selected to serve these functions, offering a level of tunability for controlling and extending drug release not possible with other technologies.

In several aspects, suitable polymers can be obtained commercially. For example, various polycaprolactone formulations can be obtained from Solvay Chemicals or Lactel (Pelham, Ala.) or Sigma Aldrich in St. Louis, Mo. (Catalog numbers 440752, 440744)

In further aspects, those of skill in the art can readily prepare polymers and copolymers by radical initiation or condensation or recombinant, vector-based synthesis of monomers corresponding to the desired polymer residues.

It is understood that the polymer can be provided as a solution, emulsion or suspension in a solvent or with surfactant stabilization, for example, during spray coating.

In some aspects synthetic polymers can be used. The following are examples of synthetic polymers: (including but not exclusive to) polyesters, polyamides, polyvinyls, polyanhydrides, polyorthoesters, polyaminoacids, polyalkenes, polyacrylates, polyarylates, polyolefins, polyacrylamides, polysugars, polyphosphonates, polyphosphazenes, polytyrosines, polyethers, polyurethanes, polycarbonates.

In some aspects natural polymers can be used. The following are examples of natural polymers: (including but not exclusive to) collagens and gelatins, silks, keratins, elastins, and their recombinant polymers and peptides, and peptide-polymer combinations, nucleic acids and their derivatives, starches including cellulose derivatives, alginates, polyhydroxyalkanoates, glycosaminoglycans, proteoglycans, fibrin glues and fibrinogen derivatives.

The bioactive agent(s) or pharmaceutically active agent(s) of the herein disclosed compositions and methods can be any such agent suitable for administration to a scaffold graft site. In some aspects, the bioactive agent or pharmaceutically active agent is selected to promote scaffold incorporation, promote tissue regeneration, prevent infection, or any combination thereof. For example, the bioactive or pharmaceutically active agent(s) can act to: control infection and inflammation; enhance cell growth and tissue regeneration; control tumor growth; act as an analgesic or anesthetic; promote anti-cell attachment; enhance bone growth; hinder osteoporosis; and enhance local anabolic or metabolic tissue functions, among other functions. Bioactive agents include prodrugs, which are agents that are not biologically active when administered but, upon administration to a subject are converted to bioactive agents through metabolism, enzymes or some other mechanism. Additionally, any of the compositions of the invention can contain combinations of two or more bioactive and pharmaceutical agents.

In some aspects, the bioactive agent or pharmaceutically active agent is present in the scaffolds in an amount necessary to provide a therapeutically effective dosage over at least one week as an extended release formulation. In some aspects, the bioactive agent or pharmaceutically active agent is present in the scaffolds in an amount necessary to provide a therapeutically effective dosage over at least two weeks. In some aspects, the bioactive agent or pharmaceutically active agent is present in the scaffolds in an amount necessary to provide a therapeutically effective dosage over at least three weeks. In some aspects, the bioactive agent or pharmaceutically active agent is present in the scaffolds in an amount necessary to provide a therapeutically effective dosage over at least four weeks. In some aspects, the bioactive agent or pharmaceutically active agent is present in the scaffolds in an amount necessary to provide a therapeutically effective dosage over at least five weeks. As disclosed herein, this extended agent release beyond the conventional initial bolus release of less than one week has specific therapeutic advantages for patient use.

In some aspects, the bioactive agent or pharmaceutically active agent is present in the scaffolds in an amount necessary to provide a therapeutically effective dosage over at least one day. In some aspects, the bioactive agent or pharmaceutically active agent is present in the scaffolds in an amount necessary to provide a therapeutically effective dosage over at least 1, 2, 3, 4, 5, 6, 7, 8, 9, 10, 11, 12, 13, 14, 15, 16, 17, 18, 19, 20 days. In some aspects, the bioactive agent or pharmaceutically active agent is present in the scaffolds in an amount necessary to provide a therapeutically effective dosage over at least one week. In some aspects, the bioactive agent or pharmaceutically active agent is present in the scaffolds in an amount necessary to provide a therapeutically effective dosage over at least two weeks. In some aspects, the bioactive agent or pharmaceutically active agent is present in the scaffolds in an amount necessary to provide a therapeutically effective dosage over at least three weeks. In some aspects, the bioactive agent or pharmaceutically active agent is present in the scaffolds in an amount necessary to provide a therapeutically effective dosage over at least four weeks. In some aspects, the bioactive agent or pharmaceutically active agent is present in the scaffolds in an amount necessary to provide a therapeutically effective dosage over at least six weeks.

Bioactive agents or pharmaceutically active agents ("agents") include the herein disclosed categories and specific examples. It is not intended that the category be limited by the specific examples. Those of ordinary skill in the art will recognize also numerous other compounds that fall within the categories and that are useful according to the invention.

It is understood that an agent can be used in connection with administration to various subjects, for example, to humans (i.e., medical administration) or to animals (i.e., veterinary administration).

In some aspects, the bioactive agent is a growth factor. It is understood that proteins such as growth factors can be naturally sourced or recombinant. In some aspects, the bioactive agent is an osteogenic growth factor. In some aspects, the bioactive agent comprises a transforming growth factor (TGF). Thus, in some aspects, the bioactive agent comprises TGF-β1. Thus, in some aspects, the bioactive agent comprises TGF-β2. Thus, in some aspects, the bioactive agent comprises TGF-β3. In some aspects, the bioactive agent comprises a bone morphogenetic protein (BMP). Thus, in some aspects, the bioactive agent comprises BMP-2. Thus, in some aspects, the bioactive agent comprises BMP-4. Thus, in some aspects, the bioactive agent comprises BMP-6. Thus, in some aspects, the bioactive agent comprises BMP-7. Thus, in some aspects, the bioactive agent comprises BMP-13. In some aspects, the bioactive agent comprises a fibroblast growth factor (FGF). In some aspects, the bioactive agent comprises an insulin-like growth factor (IGF). Thus, in some aspects, the bioactive agent comprises IGF-I. Thus, in some aspects, the bioactive agent comprises IGF-II. In some aspects, the bioactive agent comprises a platelet-derived growth factor (PDGF). Thus, in some aspects, the bioactive agent comprises PDGF-BB. In some aspects, the bioactive agent comprises a vascular endothelial growth factor (VEGF). In some aspects, the bioactive agent comprises Bone-derived growth factor-2 (BDGF II). In some aspects, the bioactive agent comprises LIM mineralization protein (LMP-1). In some aspects, the bioactive agent comprises growth differentiation factor 5 (GDF-5)). In some aspects, the bioactive agent comprises parathyroid hormone derivatives (PTH).

In some aspects, the bioactive agent or pharmaceutically active agent is an anti-inflammatory agent. Anti-inflammatory compounds include the compounds of both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desoxymethasone, desoxycorticosterone acetate, dexamethasone, dichlorisone, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, hydrocortisone acetate, hydrocortisone butyrate, methylprednisolone, triamcinolone acetonide, cortisone, flucetonide, fludrocortisone, difluorosone diacetate, fluradrenolone, fludrocortisone, difluorosone diacetate, fluocinolone, fluradrenolone acetonide, medrysone, amcinafel, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds can also be used.

Non-limiting example of non-steroidal anti-inflammatory compounds include celecoxib, nimesulide, apasone, gold, oxicams, such as meloxicam, and CP-14,304; the salicylates, such as aspirin, disalcid, benorylate, trilisate, safapryn, and solprin; the acetic acid derivatives, such as diclofenac, furofenac, acemetacin, zomepirac, clindanac, oxepinac, and ketorolac; the fenamates, such as mefenamic, meclofenamic, flufenamic, niflumic, and tolfenamic acids; the propionic acid derivatives, such as fenoprofen, indopropfen, pranoprofen, miroprofen, tioxaprofen, alminoprofen, and tiaprofenic; and the pyrazoles, such as phenylbutazone, feprazone, azapropazone, and trimethazone.

Anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Momiflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium).

In some aspects, the bioactive agent or pharmaceutically active agent is an antibiotic. Suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Thus, the bioactive agent or pharmaceutically active agent can be ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, timidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol, or any combination thereof.

In some aspects, the bioactive agent or pharmaceutically active agent is an anti-microbial peptide. Thus, the bioactive agent or pharmaceutically active agent can comprise defensin, cathelicidin, or saposin peptides and their related derivatives. Thus, the bioactive agent or pharmaceutically active agent can comprise an antimicrobial small molecule. Thus, the bioactive agent or pharmaceutically active agent can comprise benzoxazine, bipyridinium, cyanine, guanidone, naphthalimide, nitrofuran, quinazolindiamine, quinolamine, salicylanilide, or furanone or any combinations thereof.

In some aspects, the bioactive agent or pharmaceutically active agent is an anti-septic agent. Thus, the bioactive agent or pharmaceutically active agent can comprise medical alcohols (ethanol, isopropanol), chlorhexidine and related bi- and poly-guanides (e.g., PHMB), povidone iodine, triclosan and its derivatives, and cationic antiseptics including benzylakylammonium compounds, quaternary ammonium antibiotics, and antimicrobial polycations and related compounds known for anti-septic properties.

In some aspects, the bioactive agent or pharmaceutically active agent is a therapeutic antibody drug or antibody-derivative drug class agent. Thus, the bioactive agent or pharmaceutically active agent can comprise known and emerging antibody drugs as described in Dübel, Stefan (ed.), Handbook of Therapeutic Antibodies, January 2007, 1190 pages, 3 volumes, ISBN-10: 3-527-31453-9, known to produce specific, novel therapies against osteoporosis, inflammation, tumors, infection, and also promote tissue and vascular regeneration by activating novel receptor signaling pathways in tissues.

In some aspects, the bioactive agent or pharmaceutically active agent is a bisphosphonate. Thus, the bioactive agent or pharmaceutically active agent can comprise alendronate, risedronate, etidronate, ibandronate, pamidronate, zoledronate, and related compounds.

In some aspects, the bioactive agent or pharmaceutically active agent is a pro-angiogenic agent to promote therapeutic wound site angiogenesis, endothelial cell recruitment, vascular perfusion and neovascularization. Thus, the bioactive agent or pharmaceutically active agent can comprise angiogenesis promoters such as VEGF, its truncated forms and analogs, Endothelin-1, Ang-1 and -2, PDGF isoforms, and other bioactive compounds in this regard as described U.S. Pat. No. 6,284,758.

In some aspects, the bioactive agent or pharmaceutically active agent is a angiogenesis inhibitor, or anti-neoplastic or anti-tumor agent. Thus, the bioactive agent or pharmaceutically active agent can comprise any of a number of known anti-cancer drugs.

In some aspects, the bioactive agent or pharmaceutically active agent is a statin. Thus, the bioactive agent or pharmaceutically active agent can comprise lovastatin, pravastatin, simvastatin, atorvastatin, rosuvastatin, fluvastatin, and related statin derivatives.

In some aspects, the bioactive agent or pharmaceutically active agent is a transgenic bioactive molecule. Thus, the transgenic bioactive molecule can comprise a protein or peptide (e.g., an enzyme, a cytokine, a structural protein such as collagen, an antibody or other protein comprising an antibody binding site, a hormone, a detectable protein such as green fluorescent protein, a chimeric or fusion protein, a protein having a general systemic metabolic function, such as factor VIII, a virus such as a vector, etc.), a nucleic acid (e.g., a ribozyme, an antisense molecule, an aptamer, an siRNA, etc.) or a combination (e.g., a virus). Suitable bioactive molecules can further comprise compounds that cannot be encoded genetically, such as compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED and SURGICEL, available from Ethicon, Inc.), glycoproteins, glycosaminoglycans (e.g., heparin sulfate, heparin, chondroitin sulfate, dermatan sulfate, keratan sulfate, hyaluronic acid), analgesics, and compounds or agents that suppress the immune system (e.g., immunosuppressants). In one aspect, the transgenic bioactive molecule can comprise at least one of bound cytokines and free cytokines.

In some aspects, the bioactive agent or pharmaceutically active agent is an matrix-enhancing agent. In this aspect, the matrix-enhancing molecules serve to promote the increased production of ECM to induce production of matrix proteins such as, for example and without limitation, glycoproteins, elastin, and collagen, without substantially increasing cell proliferation. Thus, the bioactive agent or pharmaceutically active agent can comprise matrix-enhancing molecules (e.g., TGF-.beta, angiotensin II, insulin-like growth factors, ascorbic acid).

In some aspects, the bioactive agent or pharmaceutically active agent is a biological matrix material. In these aspects, the biological matrix material can comprise, for example and without limitation, collagen, elastin, and fibronectin.

Methods of Making

In one aspect, the invention relates to methods of preparing a scaffold disclosed herein. In some aspects, the method comprises the steps of providing a scaffold; combining an effective amount of one or more bioactive agent or pharmaceutically active agent with the substrate; and coating the scaffold with a degradable polymer.

In some aspects, the combining is soaking the scaffold in a solution comprising the agents. In some aspects, the combining and coating steps are performed substantially simultaneously by mixing the solvated polymer with both free agents and microencapsulated nanoencapsulated agent pre-formulations, and coating the mixture on the scaffold surface. In some aspects, the combining and coating steps are performed substantially simultaneously by soaking the scaffold in drug solution, impregnating the scaffold with the free or encapsulated drug, and coating the polymer containing either free or encapsulated drug particles or both over the scaffold.

As disclosed herein, the scaffolds disclosed herein provide multi-tiered nature of the therapeutic agent loading strategy, allowing for versatile tailoring of the drug selection, combination therapies, individual drug loadings and dosings, and controlled and extended release to the site of application to produce application- and even patient-specific treatment approaches. It is contemplated that the scaffolds can be seeded or otherwise loaded as desired at the time of or before implantation.

For example a scaffold can be (1) soaked directly with drug (free or microencapsulated), (2) coated with a rate-controlling biodegradable, degradable or resorbable polymeric barrier coating (e.g., polycaprolactone), which can further contain a drug or drugs formulation (free, microencapsulated or nanoencapsulated, or suspended in a secondary biodegradable polymer), and/or (3) impregnated or packed into the substrate with a synthetic or natural polymer (e.g., DBM, PRP, collagen, protein gel) throughout the porous structure of a scaffold that can also be loaded with one or multiple drugs in various physical and chemical forms. These three drug loading and dosing levels constitute the Primary Loading and Dosing Tiers.

Primary Loading and Dosing Tier (1) can be obtained by soaking the scaffold directly in a solution of either free or microencapsulated agent. Microencapsulation of the agent adds an additional level of loading and controlled release, and hence another tier to the graft system. The scaffold could then be further treated with either or both Primary Loading and Dosing Tiers (2) and (3).

Primary Loading and Dosing Tier (2) can be obtained through the polymer application strategies described herein and incorporating various drug formulations into the Tier (2) rate-controlling element itself. The agent could be free in the matrix, formulated within an interspersed microencapsulated or nanoencapsulated phase, or incorporated into a secondary polymer with a degradation rate different than that of the bulk rate modulating Tier (2) polymer. Both microencapsulation or nanoencapsulation of the agent and incorporation into a secondary differentially-degradative polymer add additional levels of controlled release, and hence additional tiers to the scaffold system. Scaffolds treated with Primary Loading and Dosing Tier (2), can also have previously been loaded under (1) and may go on to be loaded under (3), but does not necessarily require any previous or further loading; any combination is possible.

Primary Loading and Dosing Tier (3) can be obtained by packing the void space of the scaffold with either synthetic or naturally derived polymer (e.g., DBM, PRP, collagen or protein or polymer gel or carrier) containing agent. For particulate scaffolds, the pieces can be mixed with the Tier (3) polymer to make a packable paste. For non-porous scaffolds, the Tier (3) can be applied as a uniform surface coat. Agent can be added to the Tier (3) in any of the forms previously described. The agent can be free in the matrix, formulated within an interspersed microcapsule phase, or incorporated into a secondary polymer with a degradation rate different than that of the bulk rate modulating Tier (3) polymer. Both microencapsulation or nanoencapsulation of the agent and incorporation into a secondary differentially-degradative polymer add additional levels of controlled release, and hence additional tiers to the graft system. Scaffolds treated with Primary Loading and Dosing Tier (3), can have previously been loaded under (1) and/or (2), but does not necessarily have to have received any previous loading; any combination is possible.

In some aspects, the polymer has a structure and a molecular weight selected to degrade over a therapeutic time period when implanted within a subject and thereby release the agent over a corresponding time period by degradation controlled kinetics.

In some aspects, the rate-controlling polymer coating is spray coated. In some aspects, the coating is applied via soaking or dip-coating methods common to the biomedical industry. In some aspects, the mixing and coating steps are performed substantially simultaneously. In further aspects, the mixing and coating steps are performed sequentially.

Also disclosed herein are the products produced by the disclosed methods.

Experimental Examples

Scaffolds were fabricated using an SPS method. A 4% polyurethane solution was prepared by dissolving Tecoflex SG80 polyether polyurethane (Lubrizol Advanced Materials Inc. Cleveland, Ohio) in dimethylacetamide (DMAc) (Sigma Aldrich, St. Louis, Mo.). The polymer solution was sealed in glass storage containers prior to use and used immediately after opening to ensure that minimal solvent was lost through evaporation. Deionized water (referred to as 0% ethanol), 50% EtOH, and 70% EtOH solutions were used as the nonsolvent for precipitation.

Figure 1:
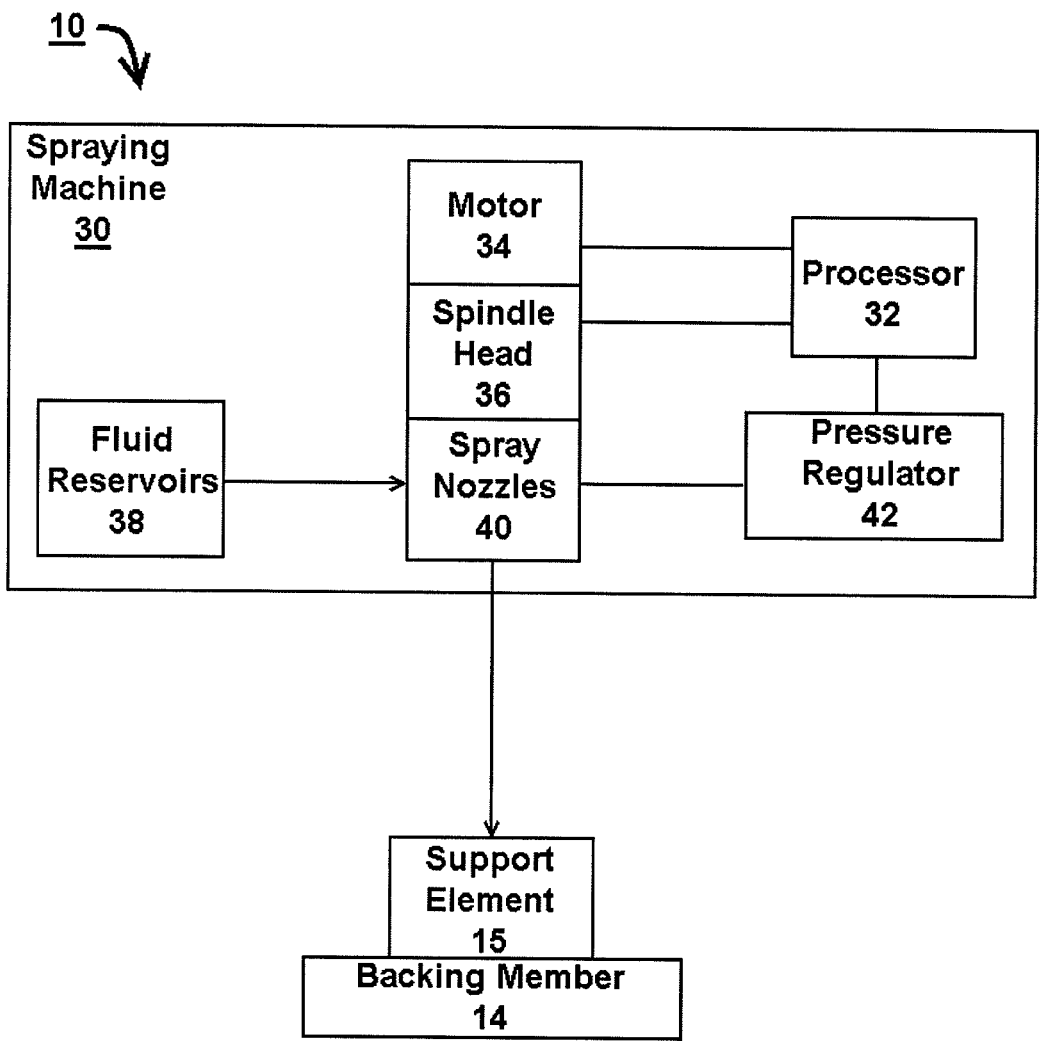
Figure 2A:
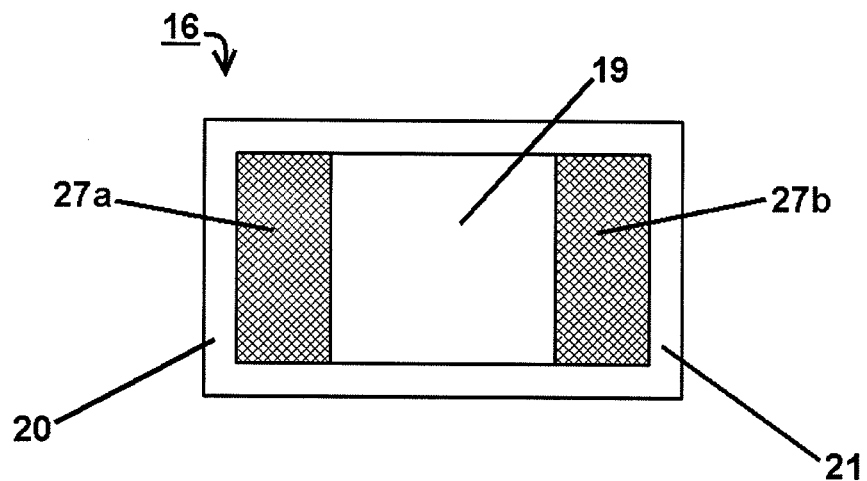
Figure 2B:
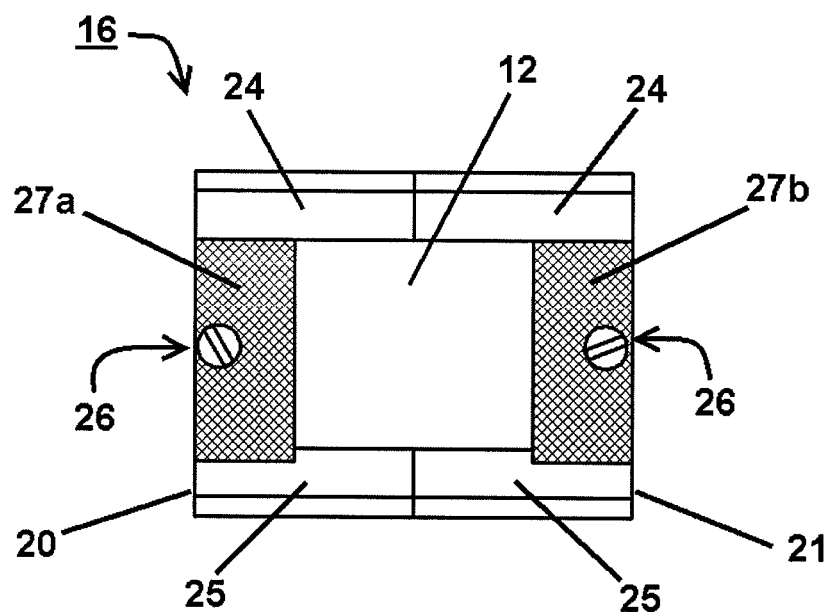
Figure 2C:
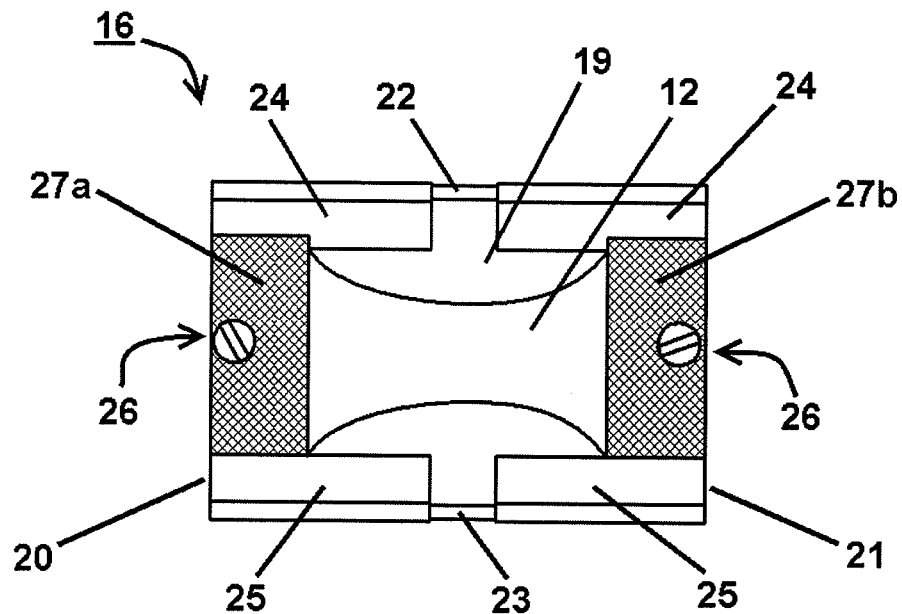
Figure 2D:
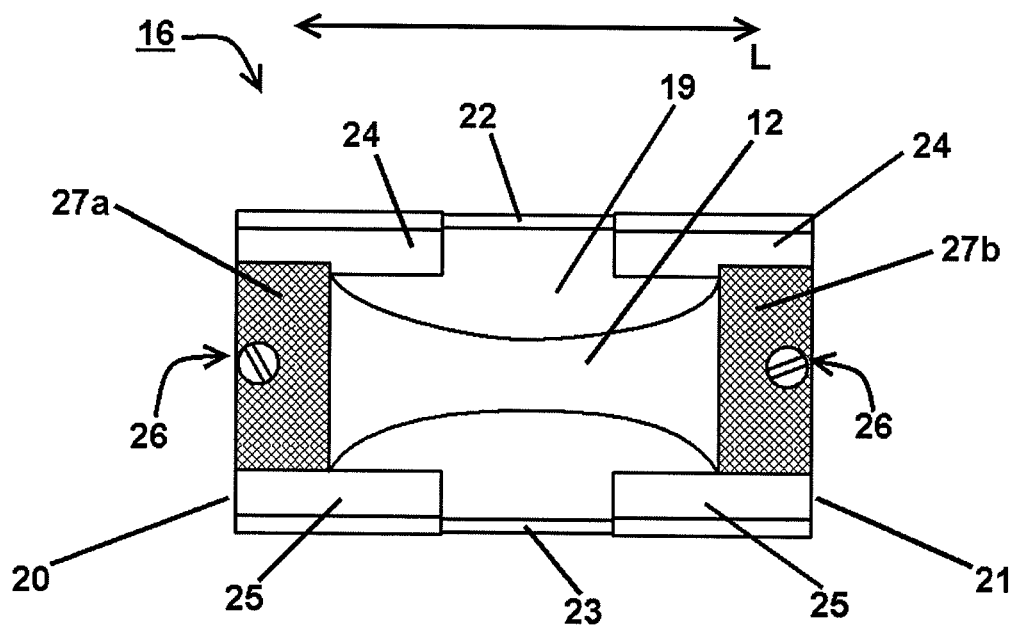

As schematically depicted in FIG. 1, spray nozzles (Excel ES4, Porter Cable, Jackson, Tenn.) were mounted onto a custom crossbar attached to the spindle head of a computer-controlled desktop milling machine (MaxNC 12, MAXNC, Gilbert Ariz.) to provide three-dimensional control of the spray pattern. Custom G-code was used to move the spray head and control the spray pattern and spray time. The spray nozzles traversed the substrate at a distance of 20 cm and a speed of 0.85 cm/s in a serpentine pattern yielding a total spray time of 2.5 minutes.

Aluminum frames were designed to facilitate manipulation and mechanical alignment of the scaffold material during and after spraying. The frames were fabricated from 0.32 cm thick 6016-T6 aluminum (McMAster-Carr, Princeton N.J.) with an outside dimension of 5.3 cm×3.7 cm and an inside dimension of 2.86 cm×2.54 cm. Stainless steel hypodermic tubing sliders (elongation guides) (Small Parts Inc., Miramar, Fla.) were assembled and attached to frames with UV cure adhesive to facilitate elongation and constrain the maximum elongation to 3.86 cm (35% elongation) or 4.86 cm (70% elongation). Frames without elongation guides were used to make scaffolds with no in-process mechanical alignment. Stainless steel screens (Type 316 Mesh #60, Small Parts Inc.) were attached to the opposite ends of the frame to provide a rigid, yet porous surface for scaffold adherence. A sheet of 0.32 cm thick aluminum (McMaster-Carr) was coated with silicone (VST 50 silicone elastomer, Factor II Inc., Lakeside, Ariz.) to prevent the scaffold from sticking to the aluminum. Three frames (one of 0%, 35% and 70% elongation) were clamped to this silicone coated aluminum backing which was subsequently placed inside the spray chamber.

The polymer solution and nonsolvent were sprayed simultaneously onto the frames at a pressure of 40 pounds per square inch. Spray rates were calculated by measuring the mass loss of the spray reservoir after a 30 second test spray. The density of the solution was used to convert the mass to volume. Spray rates of the polymer solution and the non-solvent were adjusted on the spray nozzle to 7.5±0.5 g/min and 45.0±5.0 g/min respectively to achieve uniform scaffold structure.

After the spray process was completed, scaffolds were immediately rinsed with gently flowing deionized (DI) water for 1 minute. The frames were then removed from the aluminum backing, and scaffolds were elongated 0%, 35% or 70% of their original length and allowed to dry for 24 hours in the elongated conformation. After the scaffolds were dry, they were removed from the frames for testing.

Mechanical properties were measured in the direction aligned with the in-process elongation (preferred direction) and normal (transverse) to this direction. A sample was removed from the center of each scaffold for mechanical testing (n=3). The samples used for longitudinal testing measured 20.0 mm×5.0 mm and the samples used for transverse testing measured 5.0 mm×1.5 mm. These sizes were chosen based on the physical limitations of the scaffold and frame configuration. Samples were tested on an Instron 3342 (Instron, Norwood Mass.) with a 50 N load cell. A gauge length of 10 mm was used for longitudinal testing, while a gauge length of 3 mm was used for transverse testing. The samples were tested to 40% strain at a speed of 20 min/min. The effective stress for each sample was calculated by dividing the force by the overall cross section. From the effective stress and strain data an effective modulus of elasticity was calculated in both the preferred and the transverse direction. As used herein, anisotropy refers to the ratio of the effective modulus in the preferred direction to the effective modulus in the transverse direction.

As used herein, porosity refers to the ratio of the volume of the void space of a solid to the total volume of the solid. Total volume was calculated by measuring length, width and height of rectangular scaffold samples (approximately 30×5×0.15 mm). See Papenburg B, Vogelaar L, Bolhuis-Versteeg L, Lammertink R, Stamatialis D, Wessling M. *One-step fabrication of porous micropatterned scaffolds to control cell behavior*. Biomaterials 2007; 28(11):1998-2009. The mass of the scaffold samples was then used in conjunction with the specific gravity of Tecoflex SG80 polyurethane (1.04 g/cc) to determine the volume of polyurethane in the sample. Void space volume was calculated as the difference in volume between the total volume and the volume of the polyurethane. Porosity was calculated as the ratio of void space volume to total volume of the scaffold.

Mouse embryo fibroblast NIH-3T3 cells were cultured in Dulbecco's modified Eagle medium (DMEM) with 10% fetal bovine serum (FBS) and 1% L-glutamine, and 1% penicillin and streptomycin (Invitrogen, Carlsbad, Calif.). All culture media mentioned herein are the same as described above unless otherwise noted. Cells were cultured in a T-flask (Fisher Scientific, Waltham, Mass.) and media was changed twice per week until the cells reached approximately 90% confluence. Cells were then passaged. Briefly, culture media was removed from the cells. Cells were then rinsed with sterile PBS to remove any remaining culture media. Trypsin was added to the flask, and allowed to act for 2-4 minutes at 37° C. Fresh media was then added to quench the trypsin. Cells were centrifuged and the supernatant discarded. The cell containing pellet was then resuspended in fresh media and transferred to a new T-flask. Cells were passaged three times before seeding onto the scaffold.

Prior to seeding, scaffolds were sterilized by spraying with 70% EtOH and rinsing with sterile phosphate buffered saline (PBS) and culture media. Cells were removed from the surface of the cell culture flask via trypsinization as described above. These cells were then separated from trypsin through centrifugation and re-suspended in cell culture media. Approximately $3.5 \times 10^7$ cells were seeded by gently pipetting 500 µl of the cell suspension onto the surface of the scaffold in a 100 mm plastic culture dish (Fisher Scientific). Cells were allowed to attach for two hours according to previously published methods before the scaffold was covered with fresh culture media. See Fromstein J D, Zandstra P W, Alperin C, Rockwood D, Rabolt I F, Woodhouse K A. *Seeding bioreactor-produced embryonic stem cell-derived cardiomyocytes on different porous, degradable, polyurethane scaffolds reveals the effect of scaffold architecture on cell morphology*. Tissue Eng Part A 2008 March; 14(3):369-378. Media was replaced with fresh media twice each week for 14 days.

Following cell culture, cells were imaged with fluorescein diacetate (FDA) (Invitrogen) to ensure that viable cells were present. The cells were then fixed with 4% paraformaldehyde, and stained with DAPI (Invitrogen) for nuclei visualization and phalloidin conjugated with alexafluor 488 (Invitrogen) for actin filament visualization according to the manufacture's guidelines. Images were then collected using an Olympus FV 1000 (Center Valley, Pa.) confocal microscope starting at the surface of the scaffolds, and capturing image slices every 5 µm to a depth of 50 µm. These stacks were then projected into a single image of the maximum intensity pixels through scaffold using ImageJ (NIH imaging software, Bethesda Md.).

Image analysis was performed on the projected images using custom written MATLAB code. A two-dimensional fast Fourier transform (2D FFT) method similar to what is reported by Ayres et al. was used to measure the direction of fiber alignment. See Ayres C E, Jha B S, Meredith H, Bowman J R, Bowlin G L, Henderson S C, et al. *Measuring fiber alignment in electrospun scaffolds: a user's guide to the 2D fast Fourier transform approach.* J Biomater Sci Polym Ed 2008; 19(5):603-621. Briefly, randomly selected regions of cell growth were processed with a Gaussian filter in order to reduce edge effects. A 2D FFT was performed and filtered to include only frequencies from 20-50 pixels. This range was selected based on the average spacing of actin filaments in the images in order to decrease artifacts from larger structures such as scaffolds. Average pixel intensity was measured at every angle in the frequency range mentioned above. Average pixel intensity was plotted with respect to the angle from horizontal, and shifted 90° to align the peak with the direction of actin filament alignment. Cellular alignment is reported as the orientation index, which is defined as the angle that captures 50% of the actin filament alignment, as determined by the area under the average pixel intensity curve.

In order to generate composite materials, scaffolds were laminated together during the drying process. Scaffolds were fabricated as described previously and elongated 70%. Instead of drying overnight individually, five scaffolds were placed one on top of another and allowed to dry. During the drying process the scaffolds formed a continuously adhered lamination. After the laminated scaffolds had dried, they were frozen in liquid nitrogen and broken to expose the cross section. The cross section of the composite material was observed through electron microscopy to qualitatively assess pore structure and the lamination interface.

Scaffolds were sputter coated with gold (Pelco SC-7, Ted Pella, Inc., Redding, Calif.) prior to electron microscopy and imaged using a Hitachi S-2460N (Hitachi, Tokyo, Japan) at 35× (laminated scaffold) or 200× magnification and a voltage of 10.0 kV.

A single factor analysis of variance (ANOVA) ($\alpha=0.05$) was used to compare moduli of scaffolds prepared with the same nonsolvent. A Tukey post hoc test was used to assess statistical significance. Unpaired t-tests were used to assess the statistical significance of porosity and cellular alignment.

Scaffolds of varying anisotropy were fabricated using the apparatus shown in FIG. 1. For these initial studies, nonsolvent (NS) concentrations of 0%, 50% and 70% EtOH were used. Post-spray elongation was varied at 0%, 35% and 70%. Scaffold thickness was 75±8 µm for 0% EtOH scaffolds, 167±42 µm for 50% EtOH scaffolds, and 210±11 µm for 70% EtOH scaffolds, per individual sheet. The SEM visualizations displayed in FIG. 9 revealed that scaffolds fabricated with lower NS concentrations of EtOH appeared to have fewer pores than scaffolds fabricated with higher NS concentrations of EtOH. As the percent post-spray elongation (PE) increased more elongated and aligned surface architecture was observed. Scaffolds fabricated with 50% or 70% EtOH NS were found to have microfibers oriented in the direction of elongation. Scaffolds fabricated with 0% EtOH NS did not have fibers, but did show increasing alignment of ridge-like structures as the PE increased.

Tensile testing was performed to determine the effects of PE and NS composition on the mechanical properties of the scaffolds. Testing was performed in the preferred direction (PD) and perpendicular to the direction of alignment (transverse, XD). The modulus was calculated for the linear portion of the stress-strain curve, which for all scaffolds corresponded to strains from 10-40%. As shown in FIG. 10, transverse moduli for 70% PE scaffolds were less than the longitudinal modulus ($p<0.05$), while the transverse moduli of 35% PE scaffolds were always less but not always significant. All scaffolds that were mechanically aligned showed a significant increase in longitudinal modulus between 0% and 35%, and 0% and 70% PE ($p<0.05$). All scaffolds fabricated with equal PE exhibited increasing effective moduli as the NS EtOH decreased ($p<0.05$).

Mechanical anisotropy of the scaffolds was assessed as the ratio of the longitudinal modulus to the transverse modulus. As shown in FIG. 16, for all scaffolds, the anisotropy ratio increased as the PE increased.

Porosity of the scaffolds varied with respect to the percent EtOH used in the NS. Measured porosity was independent of in-process elongation (data not shown). As shown in FIG. 11, porosity of scaffolds fabricated with 0% EtOH NS (porosity of 70±6%) was lower than those fabricated with 50% EtOH NS (porosity of 78±3%, $p=0.0006$). Scaffolds fabricated with 70% EtOH (porosity of 88±2%) had a significantly higher porosity than scaffolds fabricated with 50% EtOH NS ($p=0.00014$).

To determine the effect of the scaffold microarchitecture on cellular alignment, actin filaments of the cells were stained with phalloidin and nuclei were stained with 4',6-diamidino-2-phenylindole (DAPI). Cells were imaged at 20× magnification in order to include the largest number of cells in the field of view while maintaining sufficient resolution to image individual actin filaments. Scaffolds were imaged at 5 µm intervals from the surface of the scaffold to a depth of 50 µm. FIGS. 12A and 12B represent SEM images at 0% elongation and 70% elongation, respectively. Cells were generally observed to be aligned with scaffold filaments and along the pore edges of the material. An example of a typical 2D FFT and pixel intensity plot are shown in FIGS. 13A and 13B, respectively. As shown in FIG. 14, orientation index decreased as post-spray elongation increased ($p<0.05$). Lower orientation indices represent more aligned actin filament orientation. No significant differences were observed between 50% EtOH NS and 70% EtOH NS scaffolds of equal elongation. In summary, scaffolds with equal in-process elongation demonstrated similar alignments, regardless of porosity. Scaffolds that underwent more in-process elongation had lower orientation indices, indicating higher degrees of alignment.

Figure 15B:
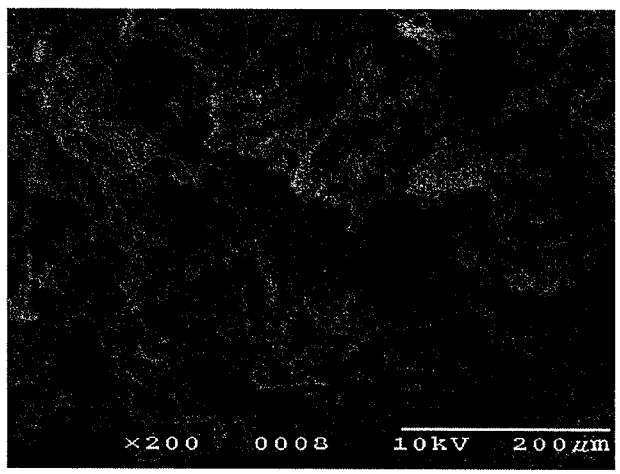

In order to generate thicker materials, scaffolds were laminated during the curing process. Scaffolds were fabricated as described previously and elongated 70%. Instead of drying overnight individually, five scaffolds were placed one on top of another and allowed to cure. During the curing process the scaffolds formed a continuously adhered lamination. After the laminated scaffolds had cured, they were frozen in liquid nitrogen and broken to expose the cross section. As shown in FIGS. 15A and 15B, the cross section of these thick scaffolds was observed through electron microscopy to qualitatively assess pore structure and the lamination interface. The overall thickness was 825±102.1 µm, and the lamination boundaries were undetectable.

Perfusion channels were created through two methods. The first method was used to create perfusion channels of relatively large diameter (300-500 µm). Individual sheets were laminated with 370 µm diameter PTFE tubes between layers. After the scaffold was cured, the tubes were removed leaving continuous channels through the scaffold Preliminary observations of flow through these channels demonstrate that they traverse the scaffold structure and are capable of flowing fluids along their entire length. The second method allowed creation of smaller diameter, more densely packed channels. A mold was designed in 3D design software (SolidWorks) with channel sizes ranging from 80 to 200 µm width and was printed using a 3D printer (Objet Geometries Inc., Billerica, Mass.). The printed mold was used to create a patterned PDMS surface. Scaffolds were sprayed onto the surface and were shown to match the pattern they were sprayed onto. Scaffolds were then laminated and allowed to cure. In order to visualize the structure of the channels, scaffolds were frozen with liquid nitrogen and then broken. The cross section of the scaffold was imaged with a stereomicroscope (Olympus, Center Valley, Pa.). It was found that about 50% of the channels had not collapsed and were intact.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method for producing at least one scaffold, comprising:
    securing at least one frame thereon a backing member, wherein an inner portion of each frame of the at least one frame defines a central opening, wherein at least a portion of each frame of the at least one frame is configured to promote adherence of a scaffold;
    simultaneously spraying a polymer solution and a non-solvent therein one or more central openings of the at least one frame such that a scaffold of the at least one scaffold is formed therein the central opening of each frame, wherein each frame comprises opposed first and second portions that define respective portions of the central opening, and wherein each scaffold is adhered to the first and second portions of each frame;
    selectively moving at least one of the first and the second portion of each frame from a closed position to an open position to elongate each scaffold by a desired length along a longitudinal axis of the frame to an elongated condition such that each scaffold develops at least one desired property; and
    removing the at least one scaffold from the at least one frame.

2. The method of claim 1, wherein the at least one scaffold is biocompatible.

3. The method of claim 1, wherein the at least one desired property comprises at least one of desired anisotropic properties, a desired cellular alignment, and a desired porosity.

4. The method of claim 1, further comprising rinsing the at least one scaffold after the step of simultaneously spraying a polymer solution and a non-solvent.

5. The method of claim 1, further comprising drying the at least one scaffold after the step of simultaneously spraying a polymer solution and a non-solvent.

6. The method of claim 1, wherein the polymer solution comprises polyether polyurethane.

7. The method of claim 6, wherein the polymer solution further comprises dimethylacetamide, and wherein the polyether polyurethane is dissolved therein the dimethylacetamide.

8. The method of claim 7, wherein the polymer solution comprises a desired amount of polyether polyurethane, wherein the desired amount of polyether polyurethane ranges from about 1% to about 10% by weight of the polymer solution.

9. The method of claim 1, wherein the non-solvent comprises deionized water.

10. The method of claim 9, wherein the non-solvent further comprises a desired amount of ethanol, and wherein the desired amount of ethanol ranges from about 0% to about 80% by weight of the non-solvent.

11. The method of claim 1, wherein the central opening of each frame of the at least one frame has a length and a width, wherein the length of each central opening ranges from about 1.25 cm to about 4.50 cm, and wherein the width of each central opening ranges from about 1.00 cm to about 4.00 cm.

12. The method of claim 1, wherein the step of elongating each scaffold comprises selectively moving at least one of the first and the second portion of each frame along a first and a second elongation guide member of the frame.

13. The method of claim 12, wherein the first and second portions of each frame each comprise a first side member and a second side member, and wherein the first and second portions of each frame are positioned in opposed relation to one another along the longitudinal axis of the frame so as to define at least a portion of the central opening.

14. The method of claim 13, wherein the first elongation guide member is attached thereto the first side members of the first and second portions of each frame, and wherein the second elongation guide member is attached thereto the second side members of the first and second portions of each frame.

15. The method of claim 14, wherein the first and second elongation guide members of each frame are substantially parallel to the longitudinal axis of each frame.

16. The method of claim 13, wherein the first and second portions of each frame further comprise a base member, wherein the first side member, the base member, and the second side member of the first portion of each frame cooperate to form a U-shape and thereby define at least a portion of the central opening of the frame, and wherein the first side member, the base member, and the second side member of the second portion of each frame cooperate to form a U-shape and thereby define at least a portion of the central opening of the frame.

17. The method of claim 16, wherein each frame of the at least one frame further comprises first and second screens, wherein the first screen is secured thereto the base member of the first portion of the frame such that at least a portion of the first screen extends into the central opening of the frame, and wherein the second screen is secured thereto the base member of the second portion of the frame such that at least a portion of the second screen extends into the central opening of the frame.

18. The method of claim 17, wherein the first and second screens of each frame comprise porous, stainless steel screens, and wherein the first and second screens are configured to promote adherence of a scaffold.

19. The method of claim 1, wherein the step of simultaneously spraying the polymer solution and the non-solvent comprises simultaneously spraying the polymer solution and the non-solvent at respective, desired spray rates.

20. The method of claim 19, wherein the desired spray rate of the polymer solution ranges from about 6.50 grams per minute to about 8.50 grams per minute, and wherein the desired spray rate of the non-solvent ranges from about 35.0 grams per minute to about 55.0 grams per minute.

21. A system for producing at least one scaffold with a polymer solution and a non-solvent, comprising:
- a backing member configured for selective positioning within a spray chamber;
- at least one frame selectively securable thereon the backing member, wherein each frame of the at least one frame has opposed first and second portions that define respective portions of a central opening, wherein the first and second portions of each frame of the at least one frame are configured to promote adherence of a scaffold, and wherein each frame of the at least one frame is selectively moveable about and between a closed position and an open position to permit elongation of a respective scaffold by a desired length such that the scaffold develops at least one desired property; and
- a spraying machine configured to simultaneously spray the polymer solution and the non-solvent therein the central opening of the at least one frame such that a scaffold of the at least one scaffold is formed therein the central opening of each frame and adhered to each frame,
- wherein the at least one frame has a higher affinity for the polymer solution and the non-solvent of the at least one scaffold than the backing member.

22. The system of claim 21, wherein the spraying machine comprises:
- a processor;
- a motor in electrical communication with the processor;
- a spindle head coupled to the motor and in electrical communication with the processor, wherein the spindle head is configured for selective three-dimensional movement;
- at least two fluid reservoirs, wherein a first fluid reservoir of the at least two fluid reservoirs contains the polymer solution, and wherein a second fluid reservoir of the at least two fluid reservoirs contains the non-solvent;
- at least two spray nozzles coupled to the spindle head, wherein a first spray nozzle of the at least two spray nozzles is in fluid communication with the first fluid reservoir, wherein a second spray nozzle of the at least two spray nozzles is in fluid communication with the second fluid reservoir, and wherein each spray nozzle of the at least two spray nozzles is configured to selectively spray fluid,
- wherein the processor is configured to:
  - activate the first and second spray nozzles to spray the polymer solution and the non-solvent at respective, desired spray rates; and
  - selectively control the three-dimensional movement of the spindle head such that the polymer solution and the non-solvent are sprayed in a desired pattern.

23. The system of claim 22, wherein the spraying machine further comprises a pressure regulator in fluid communication with the at least two spray nozzles and in electrical communication with the processor, wherein the pressure regulator is configured to selectively control the pressure at which fluid is sprayed from the at least two spray nozzles, and wherein the processor is configured to selectively control the pressures at which the polymer solution and the non-solvent are sprayed from the first and second spray nozzles.

24. The system of claim 22, wherein the spindle head comprises at least one spindle, and wherein each spray nozzle of the at least two spray nozzles is coupled to a spindle of the at least one spindle.

25. A method for producing a composite comprising a plurality of scaffolds, the method comprising:
- securing at least one support element thereon a backing member, wherein a receiving portion of each support element of the at least one support element is configured to receive a scaffold of the plurality of scaffolds;
- simultaneously spraying a polymer solution and a non-solvent therein the receiving portion of each support element of the at least one support element such that a scaffold of the plurality of scaffolds is formed therein and adhered to each respective support element; wherein each support element comprises opposed first and second support portions that define respective sections of the receiving portion, and wherein each scaffold is adhered to the first and second support portions of each support element;
- selectively moving at least one of the first and the second support portion of each support element from a closed position to an open position to elongate each scaffold of the plurality of scaffolds by a desired length along a longitudinal axis of the support element to an elongated condition such that each scaffold develops at least one desired property;
- removing the plurality of elongated scaffolds from the at least one support element;
- positioning the plurality of scaffolds in a stacked relationship such that at least one scaffold of the plurality of scaffolds is superposed relative to another scaffold of the plurality of scaffolds; and
- curing the plurality of scaffolds in the stacked relationship such that the scaffolds are connected together to form the composite.

26. The method of claim 25, wherein the step of positioning the plurality of scaffolds in a stacked relationship further comprises positioning a plurality of spaced tubular members having a selected diameter therebetween contiguous scaffolds of the plurality of scaffolds.

27. The method of claim 26, further comprising removing the plurality of spaced tubular members from the composite to thereby form a plurality of spaced perfusion channels therein the composite.

28. The method of claim 26, wherein the selected diameter of the plurality of spaced tubular members ranges from about 200 micrometers to about 600 micrometers.

29. The method of claim 26, wherein the plurality of spaced tubular members comprise polytetrafluoroethylene.

30. The method of claim 25, wherein the at least one desired property comprises at least one of desired anisotropic properties, a desired cellular alignment, and a desired porosity.

31. The method of claim 25, wherein the plurality of scaffolds comprises three or more scaffolds.

32. The method of claim 25, wherein the at least one support member comprises at least one frame, wherein the receiving portion of each frame comprises a central opening.

33. The method of claim 25, wherein the receiving portion of each support member of the at least one support member comprises at least one mold, wherein each mold comprises a corrugated outer surface, wherein the corrugated outer surface of each respective mold is configured to define a plurality of channels therein at least one scaffold of the plurality of scaffolds, wherein the plurality of channels defined therein the at least one scaffold have at least one desired property, and wherein the plurality of channels of each respective scaffold of the at least one scaffold cooperate with contiguous scaffolds to define a plurality of perfusion channels extending therethrough the composite.

34. The method of claim 33, wherein the at least one desired property of the plurality of channels defined therein each scaffold of the at least one scaffold comprise at least one of a desired width, a desired depth, and a desired spacing of channels.

35. The method of claim 33, wherein the at least one mold forms a plurality of channels therein first and second contiguous scaffolds of the composite, and wherein the plurality of channels of the first contiguous scaffold cooperate with the plurality of channels of the second contiguous scaffold to define the plurality of perfusion channels.

36. The method of claim 25, wherein the at least one support member has a higher affinity for the polymer solutions and the non-solvents of the plurality of scaffolds than the backing member.

* * * * *